(12) United States Patent
Leadbetter et al.

(10) Patent No.: US 7,335,352 B1
(45) Date of Patent: Feb. 26, 2008

(54) METHOD OF IDENTIFYING AGENTS THAT INHIBIT QUORUM SENSING ACTIVITY OF GAMMA-PROTEOBACTERIA

(75) Inventors: Jared Leadbetter, Altadena, CA (US); Jean J. Huang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 106 days.

(21) Appl. No.: 10/861,224

(22) Filed: Jun. 3, 2004

Related U.S. Application Data

(60) Provisional application No. 60/574,366, filed on May 25, 2004, provisional application No. 60/475,745, filed on Jun. 4, 2003.

(51) Int. Cl.
*A01N 63/00* (2006.01)
(52) U.S. Cl. .................................................. 424/93.4
(58) Field of Classification Search ....................... None
See application file for complete search history.

(56) References Cited

OTHER PUBLICATIONS

Lin et al, "Acyl-homoserine lactone acylase from Ralstonia strain XJ12B represents a novel and potent class of quorum-quenching enzymes." (Molecular Microbiology), vol. 47, No. 3, Feb. 2003, p. 849-860.*

Stover et al, "Complete genome sequence of *Pseudomonas aeruginosa* PAO1, an opportunistic pathogen," (Nature), vol. 406, Aug. 31, 2000, p. 959-964.*
Lamont and Martin, "Identification and Characterization of Novel Pyoverdine Synthesis Genes in *Pseudomonas aeruginosa*," Microbiology, vol. 149, pp. 833-842 (2003).
Leadbetter and Greenberg, "Metabolism of Acyl-Homoserine Lactone Quorum-Sensing Signals by Variovorax Paradoxus," Journal of Bacteriology, vol. 182, No. 24, pp. 6921-6926, Dec. 2000.
Ochsner et al., "GeneChip Expression Analysis of the Iron Starvation Response in *Pseudomonas aeruginosa*: Identification of Novel Pyoverdine Biosynthesis Genes," Molecular Micobiology, vol. 45, No. 5, pp. 1277-1287, Sep. 2002.
Whiteley et al., "Identification of Genes Controlled By Quorum Sensing in *Pseudomonas aeruginosa*," Proceedings of the National Academy of Sciences USA, vol. 96, No. 24, pp. 13904-13909, Nov. 23, 1999.
Zhang et al., "Genetic Control of Quorum-Sensing Signal Turnover in *Agrobacterium tumefaciens*," Proceedings of the National Academy of Sciences USA, vol. 99, No. 7, pp. 4638-4643, Apr. 2, 2002.

* cited by examiner

*Primary Examiner*—Robert B. Mondesi
*Assistant Examiner*—Amanda P. Wood
(74) *Attorney, Agent, or Firm*—DLA Piper US LLP

(57) ABSTRACT

Screening assays that allow for the identification of agents that increase acyl homoserine lactone (AHL) acylase expression and/or AHL acylase activity in γ-proteobacteria such as *Pseudomonas aeruginosa*. Such agents are useful, for example, for inhibiting quorum sensing activity of such bacteria by increasing degradation of long chain, but not short chain, AHLs and, therefore, can be useful for treating infections by such bacteria.

23 Claims, 7 Drawing Sheets

METHOD OF IDENTIFYING AGENTS THAT INHIBIT QUORUM SENSING ACTIVITY OF GAMMA-PROTEOBACTERIA

CROSS REFERENCE TO RELATED APPLICATIONS

This application claims the benefit of priority under 35 U.S.C. § 119(e) of U.S. Ser. No. 60/475,745, filed Jun. 4, 2003, and of U.S. Ser. No. 60/574,366 (Caltech Ref. No. 4113-P), filed May 25, 2004 (entitled "The protein encoded by gene Pa1032 is expressed during the degradation of long acyl chain acyl-homoserine lactones by *P. aeruginosa* and exhibits a potent acyl-homoserine-lactone degrading activity"), the entire content of each of which is incorporated herein by reference.

GRANT INFORMATION

This invention was made with government support under Grant No. DBI-0107908 awarded by the National Science Foundation. The United States government has certain rights in this invention.

BACKGROUND OF THE INVENTION

1. Field of the Invention

The invention relates generally to screening assays, and more specifically to methods of identifying agents that can modulate the expression and/or activity of an acyl homoserine lactone (AHL) acylase that breaks down long chain AHLs, but not short chain AHLs, in γ-proteobacteria such as *Pseudomonas aeruginosa*, to agents identified by such methods, and to methods of using the agents to treat a γ-proteobacteria infection by inhibiting quorum sensing activity by the bacteria.

2. Background Information

*Pseudomonas aeruginosa*, an opportunistic pathogen, is a gram-negative γ-proteobacteria. *P. aeruginosa* can thrive in a variety of environments, requiring only minimal nutrients and moisture. For example, *P. aeruginosa* exists in soil, water, and on animals. *P. aeruginosa* releases enzymes such as an elastase, an alkaline protease, and a cytotoxin that aid in the invasion and destruction of host tissues. In an infected host, *P. aeruginosa* often invades small arteries and veins, which frequently leads to metastatic nodular lesions in the lungs. *Pseudomonas* infections can be aggressive, often result in sepsis, and are associated with a high mortality rate.

Immunocompromised individuals such as patients with burns, urinary tract infections, or cystic fibrosis are particularly susceptible to *Pseudomonas* infections. In cystic fibrosis patients, for example, pneumonia due to *P. aeruginosa* infection is common, likely due to accumulated bronchial secretions providing an environment in which the *Pseudomonas* can flourish. Further, *P. aeruginosa* is extremely resistant to antibiotics and, therefore, treatment must be aggressive and, nevertheless, is often unsuccessful. Thus, a need exists for drugs that can be used to successfully treat *Pseudomonas* infections. The present invention satisfies this need, and provides additional advantages.

SUMMARY OF THE INVENTION

The present invention is based, in part, on the discovery that γ-proteobacteria such as *Pseudomonas aeruginosa* express an acyl homoserine lactone (AHL) acylase that can degrade long chain, but not short chain, AHLs to produce fatty acid and homoserine lactone (HSL), and that such AHL acylase activities can regulate quorum sensing activity in the γ-proteobacteria. As such, the invention provides methods to identify agents that can modulate γ-proteobacterium AHL acylase expression and/or activity, including high throughput screening methods, and further provides a means to identify agents that are useful for treating patients having, for example, a *Pseudomonas* infection, including agents that are useful for a particular patient, thus allowing for personalized medicine.

Accordingly, the present invention relates to a method of identifying an agent that modulates γ-proteobacterium long chain AHL acylase expression and AHL acylase activity. Such a method can be performed, for example, by contacting at least one sample (e.g., 1, 2, 3, 4, 5, etc.), which contains (or to which is/are added) the AHL acylase and a long chain AHL, with a test agent, under conditions suitable for AHL acylase activity, and detecting a change in AHL acylase activity in the presence of the test agent as compared to the AHL acylase activity in the absence of the test agent, wherein a change in AHL acylase activity identifies the test agent as an agent that modulates the γ-proteobacterium long chain AHL acylase activity. A method of the invention can be used to identify an agent that increases AHL acylase activity or an agent that decreases AHL acylase activity, as well as an agent that increases expression of an AHL acylase gene in a γ-proteobacterium (e.g., PvdQ gene expression in *P. aeruginosa*), thereby increasing AHL acylase levels and AHL acylase activity, or an agent that decreases AHL gene expression in a γ-proteobacterium.

The long chain AHL for which AHL acylase activity is examined can be any long chain AHL that can be degraded by the AHL acylase to a fatty acid and HSL, including, for example, N-3-octanoyl-DL-homoserine lactone (C8HSL), N-3-decanoyl-DL-homoserine lactone (C10HSL), N-3-dodecanoyl-DL-homoserine lactone (C12HSL), N-3-oxododecanoyl-L-homoserine lactone (3OC12HSL), or N-3-tetradecanoyl-DL-homoserine lactone (C14HSL). The γ-proteobacterium that contains the AHL acylase, or from which the AHL acylase is derived, can be any γ-proteobacterium of interest, including, for example, medically important γ-proteobacterium such as a *Pseudomonas* species (e.g., *P. aeruginosa*), a *Vibrio* species (e.g., *V. cholerae*), or an *Azotobacter* species. For example, the AHL acylase can be *Pseudomonas aeruginosa* PvdQ AHL acylase, which has an amino acid sequence as set forth in SEQ ID NO:2, or a *Pseudomonas* PA1032 AHL acylase, which has an amino acid sequence as set forth in SEQ ID NO:4 or SEQ ID NO:5.

In one aspect of a method of the invention, the sample can further contain (or have added thereto) a short chain AHL. As disclosed herein, the γ-proteobacterium AHL acylase lacks the ability to metabolize (degrade) short chain AHLs. As such, this aspect of a method of the invention provides a means to confirm that a test agent that, for example, increases AHL acylase activity with respect to long chain AHL breakdown, has no effect on the short chain AHL (i.e., by detecting no change in the amount of the short chain AHL in the presence of the test agent as compared to the absence of the test agent). A short chain AHL useful in this aspect can be any short chain AHL that is not normally degraded by the AHL acylase being examined, including, for example, N-3-butanoyl-DL-homoserine lactone (C4HSL), N-3-hexanoyl-L-homoserine lactone (C6HSL), N-3-oxohexanoyl-L-homoserine lactone (3OC6HSL), or N-3-heptanoyl-DL-homoserine lactone (C7HSL).

A sample examined according to a method of the invention can be any sample that contains (or to which can be added) an AHL acylase, such that conditions are suitable for AHL acylase activity. Such conditions, which can include, for example, an appropriate concentration of iron ions, are selected based on whether the assay is performed in a cell free format (e.g., using purified reactants such as purified AHL acylase and/or purified long chain AHLs, etc.) or is performed using a cell based assay. Accordingly, in one embodiment, the method is performed in vitro, wherein the AHL acylase comprises purified AHL acylase, which can be obtained, for example, from an extract comprising a γ-proteobacterium that expresses the AHL acylase (e.g., an extract comprising a Pseudomonas species such as P. aeruginosa), or from an in vitro translation or coupled transcription/translation reaction using a polynucleotide encoding the AHL acylase (e.g., a polynucleotide as set forth in SEQ ID NO:1 or in SEQ ID NO:3).

In another embodiment, the method is performed as a cell based assay, wherein the sample comprises a cell sample, or an extract of a cell, and wherein the AHL acylase is expressed in the cell. The cell can be a γ-proteobacterium, in which the AHL acylase is expressed in nature (e.g., a Vibrio species such as V. cholerae), can be a host cell or tissue sample that is infected with γ-proteobacteria (e.g., a biopsy sample from a subject infected with the bacteria), or can be a cell that has been genetically modified to express a polynucleotide encoding a γ-proteobacterium AHL acylase (e.g., a host cell transformed, transfected or transduced with a polynucleotide encoding a Pseudomonas PA1032 AHL acylase as set forth in SEQ ID NO:4 or SEQ ID NO:5). In one aspect of this embodiment, the sample comprises a cell, tissue or biologic fluid obtained from a subject having a γ-proteobacterium infection. In another aspect, the sample comprises a cell, tissue or biologic fluid obtained from a subject having a Pseudomonas infection. The subject can be any subject susceptible to infection by the γ-proteobacterium, including any vertebrate such as a mammal (e.g., a human subject infected by P. aeruginosa or V. cholerae).

According to the present methods, a change in AHL acylase activity can be detected using any assay suitable for measuring AHL acylase activity, including, for example, assays that can measure AHL levels and or AHL breakdown products such as a fatty acid and/or homoserine lactone (HSL) in the sample (or an aliquot or fraction of the sample). Such methods can be based on the chemical structure of the substrate (long chain AHL) and/or product (e.g., HSL) of the AHL acylase, including, for example, mass spectroscopy, which can measure the amount of AHL and/or HSL in the sample, and thin layer chromatography, which can measure the amount of HSL in the sample. AHL acylase activity can also be measured using a functional (e.g., biological) assay, including, for example, contacting the sample or an aliquot or fraction of the sample with a γ-proteobacterium (e.g., a Pseudomonas species) and detecting the amount of quorum sensing activity, or can be measured using an available bioassay strain that can be used to detect and determine the concentration of AHLs.

In one embodiment, a method of the invention is performed in a high throughput format, thus allowing for the screening, in parallel, of one or more test agents with one or more samples, wherein the agents and/or samples independently are the same or different. As such, the method allows for testing one or more concentrations of one or more test agents to identify a concentration of an agent particularly useful for modulating AHL acylase activity. Further, the method allows for examining several same test agents on one or a plurality of same samples, and/or one or more different test agents on several same samples, thus providing a means to obtain statistically significant results. Also, the method allows for examining one or a plurality of cell sample(s) taken from a subject having a γ-proteobacterium (e.g., P. aeruginosa) infection with one or a plurality of the same (e.g., different concentrations) or different test agents, to identify an agent that is best suited, for example, for increasing AHL acylase activity in the patient, thus increasing the rate of breakdown of long chain AHLs produced by the γ-proteobacterium. Such an agent can be useful for reducing or inhibiting quorum sensing activity by the infecting bacteria, thereby ameliorating the infection in the subject.

The screening assays of the invention, particularly when utilized in a high throughput format, provide a means to screen one or more libraries of test agents, including, for example, a combinatorial library of test agents, which can be a random library, a biased library, or a variegated library of test agents. For example, the method can be used to screen a combinatorial library of randomly generated test agents, then, if desired, positive agents that desirably modulate AHL acylase activity (e.g., increase AHL acylase activity) can be used to generate a library of biased and/or a variegated test agents based on the structure of the identified positive agent(s) to obtain an agent that modulates the AHL acylase activity and, for example, has additional desirable properties such as enhanced stability in a biological system (e.g., a subject to be treated with the agent), useful absorption characteristics, or the like.

The present invention also relates to an agent identified by a method of the invention. Such an agent can be, for example, a peptide, a polynucleotide, a small organic molecule, or a peptidomimetic. Where the agent is to be used for a therapeutic method, it can be formulated in a form suitable for administration to a subject, for example, as a pill or a liquid, and can be administered, for example, orally, by injection, or via inhalation. Accordingly, methods are provided for treating a subject infected with a γ-proteobacterium (e.g., P. aeruginosa) by administering an agent identified by a screening assay of the invention to the subject.

BRIEF DESCRIPTION OF THE DRAWINGS

FIGS. 3A to 3D show LC/APCI-MS analysis of a cell-free fluid sampled from a P. aeruginosa culture utilizing C10HSL as a sole energy source in MES 5.5 medium.

FIG. 3A shows a chromatogram showing the separation of homoserine and/or HSL, MES buffer, and decanoyl-HSL (left axis). The hatch marks correspond to changes in methanol/water solvent ratios during the course of the run (right axis).

FIG. 3B shows the mass spectrum of the first peak, which resolves homoserine from homoserine lactone. The peak tail can overlap with, but can be resolved from, the component in the second peak.

FIG. 3C shows the mass spectrum of the second peak, morpholinoethane sulfonic acid (MES buffer).

FIG. 3D shows the mass spectrum of the third peak, decanoyl-HSL. This method can be applied to separate and determine the concentrations of a number of other AHLs and any acyl-homoserine degradation products.

DETAILED DESCRIPTION OF THE INVENTION

Figure 1:
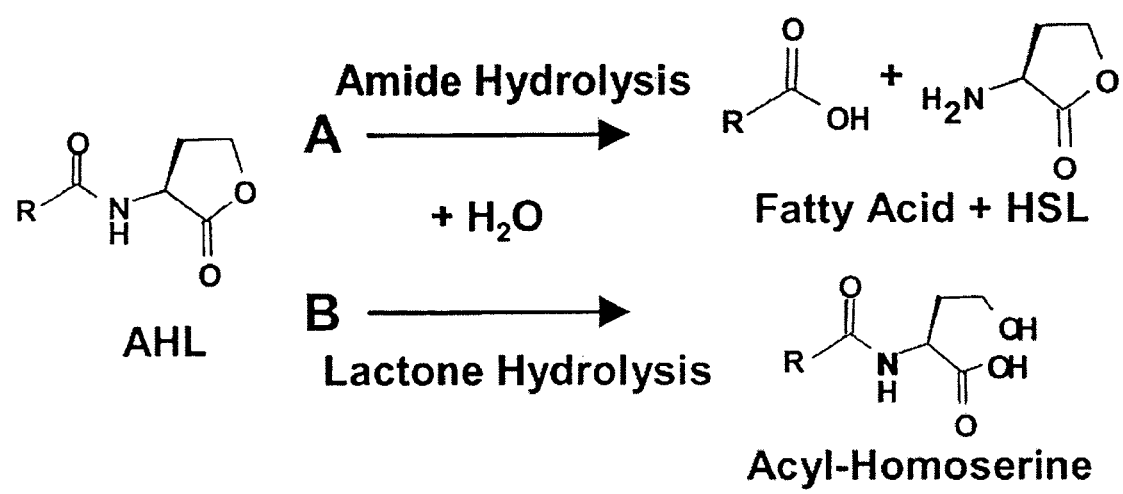
FIG. 1 depicts two mechanisms by which AHLs can be inactivated. Mechanism A represents cleavage of the amide bond by bacterial AHL acylase, which yields HSL and the corresponding fatty acid (21, 23). The AHL amide bond is chemically stable under conditions of nonextreme temperature and pH. Mechanism B represents cleavage of the lactone ring by bacterial AHL lactonase, yielding the corresponding acyl-homoserine (7, 46). The lactone ring is also subject to chemical hydrolysis; the chemical half-life of the ring is about $10^{(7-pH)}$ days, i.e., it is less stable with increased alkalinity. The acyl side chain diversity of known, naturally occurring AHLs has been reviewed (11).

The present invention is based, in part, on the discovery that γ-proteobacteria such as Pseudomonas aeruginosa ($P.$ aeruginosa) express an AHL acylase that can degrade long chain, but not short chain, acyl homoserine lactones (AHLs) to produce fatty acid and homoserine lactone (HSL), and that such AHL acylase activity regulates quorum sensing activity in γ-proteobacteria. Acyl-homoserine lactones (AHLs) are employed by several Proteobacteria as quorum sensing signals. Past studies established that these compounds are subject to biochemical decay and can be used as growth nutrients. As disclosed herein, a soil bacterium, Pseudomonas strain PAI-A, was isolated. Pseudomonas strain PAI-A degraded N-3-oxododecanoyl-L-homoserine lactone (3OC12HSL) and other long chain acyl, but not short chain acyl AHLs as sole energy sources for growth.

The small sub-unit rRNA gene from strain PAI-A was 98.4% identical to that of $P.$ aeruginosa, but the soil isolate did not produce obvious pigments or AHLs or grow under denitrifying conditions or at 42° C. The quorum sensing bacterium $P.$ aeruginosa, which produces both 3OC12HSL and C4HSL, was examined for the ability to utilize AHLs for growth, and like PAI-A, used AHLs for growth, showing a similar specificity for the degradation of long acyl, but not short acyl AHLs. In contrast to strain PAI-A, $P.$ aeruginosa PAO1 growth on AHLs commenced only after a long lag phase. Liquid chromatography-atmospheric pressure chemical ionization-mass spectrometry (LC/APCI-MS) analyses indicated that strain PAO1 degraded long acyl AHLs via an AHL acylase and a homoserine-generating HSL lactonase (see Example 1). A $P.$ aeruginosa gene, PvdQ (PA2385), was previously identified as a homologue of the AHL acylase described from a Ralstonia species. As disclosed herein, $E.$ coli expressing PvdQ catalyzed the rapid inactivation of long acyl AHLs and the release of HSL (see Example 2). $P.$ aeruginosa engineered to constitutively express PvdQ did not accumulate its 3OC12HSL quorum signal when grown in rich media. However, PvdQ knockout mutants of $P.$ aeruginosa utilized 3OC12HSL at wild-type growth rates and yields.

The present results demonstrate that pseudomonads or other γ-proteobacteria degrade AHLs, that quorum sensing bacterium have AHL acylase activity, that bacteria have HSL lactonase activity, and that AHL degradation by γ-proteobacteria is specific for AHLs with long side chains. Accordingly, the present invention provides methods to identify agents that modulate γ-proteobacteria long chain AHL acylase activity. In addition, the present invention provides compositions containing agents identified by such a method.

Many bacterial species control and modulate their physiology in response to increases in their population densities in a process known as quorum sensing (12, 25). Several dozen species of Proteobacteria use AHLs as dedicated signal molecules in this process. A diversity of acyl-HSL structures and the enzymes and proteins involved in their synthesis and recognition have been elucidated (13, 27, 31, 35). One of the best studied quorum sensing species is the opportunistic pathogen Pseudomonas aeruginosa, which makes and responds to two distinct acyl-homoserine lactones: N-3-oxododecanoyl-L-homoserine lactone (3OC12HSL; also known as PAI, the Pseudomonas autoinducer of the las QS system), and N-3-butanoyl-DL-homoserine lactone (C4HSL; also known as PAI-2, the autoinducer of the rhl QS system). The two quorum circuits control several physiologies and virulence factors associated with the infection of immunocompromised individuals, such as those with cystic fibrosis (40). The influence of AHLs on the global regulation of gene expression by $P.$ aeruginosa is vast (37, 42). AHL-mediated signaling and signal dynamics are very important to the biology of this species, and, therefore, it is important to understand issues relating to signal stability so that methods can be developed for modulating quorum sensing activity.

Quorum sensing activity provides a means of cell-to-cell communication ("cell-to-cell signaling"). A "quorum" generally comprises a dense population of cells having the capability to communicate with each other. A quorum of bacterial cells have the ability to "sense" their density level and, as a result, can act as a group of cells rather than as individual cells (see, e.g., Fuqua and Greenberg, Molecular Cell Biology Vol. 3: 685-695, Nature Reviews 2002; Van Delden and Iglewski, *Emerging Infectious Diseases* Vol. 4, No. 4: 1-10, 1998; each of which is incorporated herein by reference). Degradation of long chain AHLs hinders bacterial quorum sensing activity that would otherwise serve to exacerbate γ-proteobacteria infection in a subject.

The screening assays of the invention allow the identification of agents that modulate γ-proteobacterium AHL acylase activity by increasing AHL acylase gene expression and/or AHL acylase activity, thereby increasing the degradation of long chain AHLs. Where an agent increases (or decreases) AHL acylase gene expression, the increased (or decreased) expression results in increased (or decreased) AHL acylase levels and AHL acylase activity. As such, an agent that increases AHL acylase gene expression and/or AHL acylase activity, when administered to a subject, can decrease virulence of the bacteria expressing the AHL acylase in the subject. The subject can be any subject affected by γ-proteobacteria infections, for example, an immunocompromised human subject, or an individual suffering from cystic fibrosis or other disease that renders the subject susceptible to infection by γ-proteobacteria.

According to a method of the invention, a change in AHL acylase activity can be detected using any assay suitable for measuring AHL acylase activity, including, for example, assays that can measure AHL levels and/or AHL breakdown products such as a fatty acid and/or HSL in the sample (or an aliquot or fraction of the sample). Examples of methods useful for measuring a change in AHL acylase activity are provided, including mass spectroscopy and thin layer chromatography, which can detect levels of the AHL acylase substrate (AHL) and/or product (e.g., HSL), and additional methods for measuring AHL acylase activity (e.g., enzyme kinetics assays) are well known in the art. In addition, a biological assay based, for example, on quorum sensing activity of a medium containing the AHL acylase before and after contact with a test agent can be used to measure a change in AHL acylase activity.

The screening assays of the invention also allow the identification of an agent that decreases AHL acylase gene expression and/or AHL acylase activity, thereby decreasing breakdown of long chain AHLs. For example, certain bacteria utilize quorum sensing to regulate the production of plant protecting antifungal compounds (e.g., in suppressing fungal disease that impacts wheat roots). Agents that reduce or inhibit AHL degradation can be useful for boosting and improving quorum sensing of such beneficial bacteria, which often are used in "biocontrol" agricultural regimes.

Acyl-homoserine lactones are chemically inactivated via alkaline hydrolysis, yielding the cognate acyl-homoserine (41), but are stable for weeks or months at pH values of 5 to 6 (34). AHLs are also subject to biological inactivation (see FIG. 1). Similar to abiotic ring hydrolysis, acyl-homoserine can be generated by acyl-HSL lactonases encoded by *Bacillus cereus* (and its close relatives) and by *Agrobacterium tumefaciens* (6, 8, 22, 32, 46). None of these strains has been found to further degrade the molecule, and no net oxidation occurs during this inactivation reaction. More complete degradation can occur as evidenced by an *Arthrobacter* soil isolate that utilizes the acyl-homoserine degradation products of AHL ring hydrolysis reactions (10). In another mechanism of AHL inactivation, the amide bond of AHL is cleaved by AHL acylases during the utilization of quorum signals as growth nutrients by *Variovorax* and *Ralstonia* species (21, 23). Homoserine lactone is released as a product of these reactions and the acyl-moiety is further metabolized as an energy substrate (19, 21). When a gene encoding an AHL acylase from *Ralstonia* (AiiD) was expressed in *E. coli* and in *P. aeruginosa*, it effectively inactivated endogenously produced AHL quorum signals and quenched quorum sensing in *P. aeruginosa* (23).

A close homologue of the *Ralstonia* AHL acylase was identified in *P. aeruginosa* PAO1 and in the genomes of several other sequenced pseudomonads (23), which often produce AHLs and engage in quorum sensing. As disclosed herein, the *P. aeruginosa* PAO1, as well as a newly isolated *Pseudomonas* strain, PAI-A, utilized 3OC12HSL as an energy source, and exhibited growth on long chain acyl AHLs. Further, *P. aeruginosa* PvdQ, which is a *Ralstonia* AiiD homolog, was found to have AHL acylase activity with respect to long chain, but not short chain, AHLs.

The soil pseudomonad, strain PAI-A, was enriched and isolated, based on its ability to degrade 3OC12HSL, which is a virulence factor that is produced by and used as a dedicated signal in the quorum sensing physiology of the opportunistic pathogen *P. aeruginosa*. Subsequently, it was ascertained that two clinical strains of *P. aeruginosa* were capable of degrading and growing on 3OC12HSL and other long-acyl AHLs (see Example 1). None of the pseudomonads examined degraded either C4HSL, the other distinct AHL quorum signal produced by *P. aeruginosa*, or other short acyl AHLs tested. Although closely related to *P. aeruginosa*, strain PAI-A is a separate species, as it did not produce pigments, acyl-HSLs, or grow at 42° C. or anaerobically with nitrate as terminal electron acceptor.

Using a refined LC/APCI-MS technique, the soil and clinical pseudomonads were shown to degrade AHLs via an HSL-releasing activity, indicating that these pseudomonads use an AHL acylase in the initial step of AHL degradation, similar to the mechanism described in *Variovorax* and *Ralstonia* isolates (21, 23). *P. aeruginosa* accumulated HSL as a transient intermediate during degradation of long chain AHLs, and the HSL was subsequently delactonized to form homoserine, which was consumed (see FIG. 4). Since the culture pH was well controlled in order to preclude the chemical hydrolysis of lactone ring, the observed HSL degradation was due to a biological, and not to an abiotic, hydrolysis event. Enzymes with HSL lactonase activity are expressed in fungal and mammalian biota (15, 17). However, neither HSL nor homoserine was used as an energy or nitrogen source by *P. aeruginosa*, as they are by *Variovorax* and *Arthrobacter* species (10, 21). The HSL lactonase and homoserine degrading activities may serve as detoxification mechanisms, since both of these compounds are known to be toxic to diverse biota (10, 14, 15, 45).

There are notable differences between AHL utilization by the pseudomonads and *Variovorax paradoxus* and *Ralstonia* strain XJ12B. *Ralstonia* was reported to degrade and grow equally rapidly with short and long acyl AHLs (23). *Variovoras paradoxus* was reported to utilize the entire spectrum of short and long acyl AHLs tested, and grew most rapidly with N-3-oxohexanoyl-L-homoserine lactone (3OC6HSL, see ref. 21). Moreover, *Variovorax* exhibited molar growth yields that corresponded well with the acyl length of a given AHL. As disclosed herein, however, pseudomonads did not degrade AHLs with acyl side chains shorter than eight carbons, and no correspondence was observed between molar growth yields and AHL acyl side chain lengths (Table 1; see below), although a correspondence was observed when the cells were grown with long chain fatty acids.

Acyl homoserine lactone utilization by *P. aeruginosa* exhibited another key difference from *Variovorax, Ralstonia*, and even *Pseudomonas* strain PAI-A. When cultures not previously grown on AHL were inoculated into long acyl AHL containing media, it generally took one to three weeks before logarithmic growth commenced. However, no lag was observed when AHL grown cells were subcultured into such medium. This adaptation does not appear to reflect a stable mutation, as long lags were again observed if the subculturing process was punctuated with a transfer into or onto media containing a different energy substrate. The long initial lag time suggests that AHL degradation by *P. aeruginosa* is not immediately induced by the quorum signal, and is not controlled as a function of the catabolic needs of the cell or by cell starvation.

*Agrobacterium tumefaciens* degrades N-3-oxo-octanoyl-L-homoserine lactone (3OC8HSL), its AHL quorum signal, during early stationary phase (46). The disclosure that *P. aeruginosa* can degrade one, but not the other, of its two AHL quorum signals has revealed a previously undescribed AHL degradation apparatus. Signal decay, in addition to providing utilizable nutrients, can be involved in the regulation of the LasR/LasI/3OC12HSL-controlled quorum sensing regulon. The two principal AHL quorum signals of *P. aerugitiosa*, C4HSL and 3OC12HSL, are present in the sputum of cystic fibrosis patients and in laboratory biofilms at ratios quite different from those encountered in planktonic, liquid grown cultures. Sputum and biofilm samples contained significantly higher levels of C4HSL with respect to 3OC12HSL. Based on the present results, the different levels of the short chain C4HSL and long chain 3OC12HSL are likely due to biochemical turnover of the long chain AHL.

Figure 5:
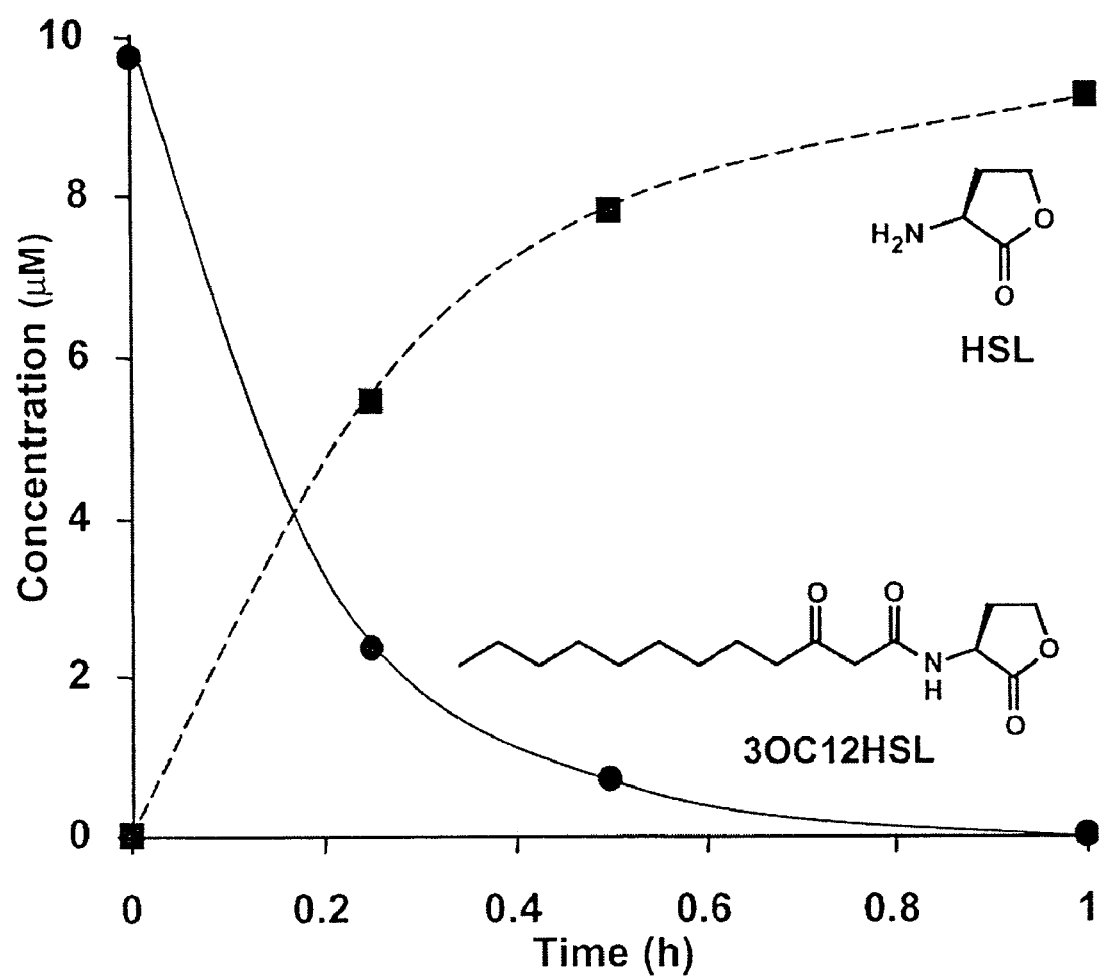
FIG. 5 shows activity of $E.$ coli cells expressing recombinant PvdQ (SEQ ID NO:2), which degraded 3OC12HSL and generated stoichiometric amounts of HSL. Substrate disappearance and product accumulation were determined by LC/APCI-MS. Induced cells containing the pPvdQ-PROTet plasmid were washed and suspended in MOPS (pH 7.2) buffered medium to a final $OD_{600}$ of 1.2. AHL degradation and HSL accumulation were not observed over the duration of the experiment in either heat-killed suspensions of the same cells, or in no-cell controls.
Figure 6:
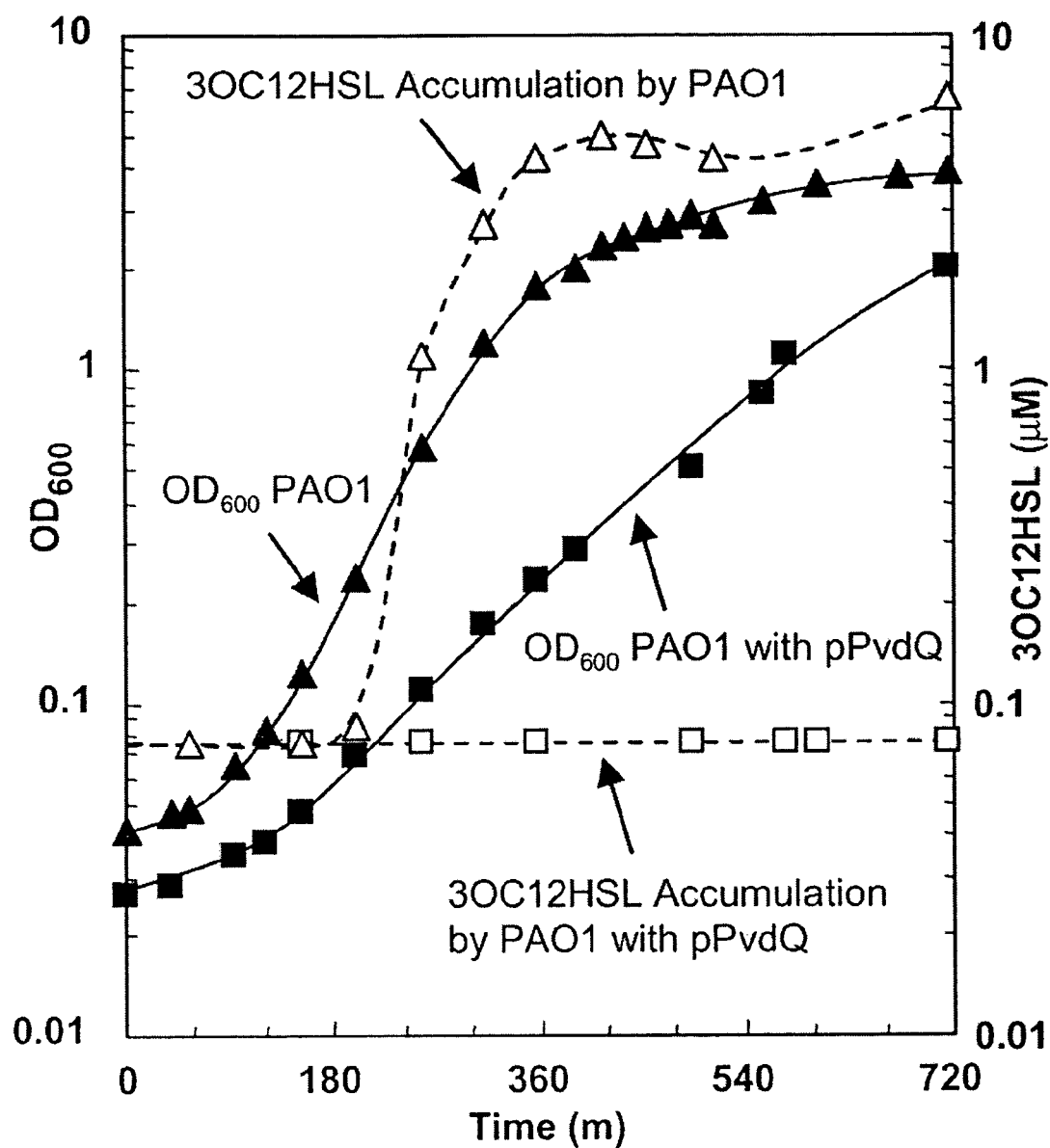
FIG. 6 shows growth and accumulation of endogenous 3OC12HSL by $P.$ aeruginosa PAO1 wild type (▲, △), and a recombinant derivative constitutively expressing PvdQ (■, □). Because of the organic complexities of LB, sampled cell-free culture fluids were extracted with ethyl acetate before LC/APCI-MS analysis; the limit of detection for 3OC12HSL was 75 nM and was plotted in place of zero. Cultures were grown at 30° C. in LB. Under similar culture conditions, a PvdQ knockout mutant grew and accumulated 3OC12HSL in parallel with the wild type.

The *Ralstonia* AiiD enzyme inactivates long chain and short chain AHLs (23). Heterologous expression of PvdQ, which is the closest homolog of the Ralstonia acylase encoded by *P. aeruginosa*, in *E. coli* conferred AHL-acylase activity specific towards long acyl, but not short acyl, chain, AHLs (FIG. 5). Expression of the PvdQ gene in *P. aeruginosa* is well regulated. The PvdQ gene was identified as being a late responder to the 3OC12HSL quorum sensing circuit (see ref. 43, which refers to the PvdQ gene as QSC 112a and QSC 112b), although gene microarray studies have not provided further support for this observation (37, 42). *P. aeruginosa* gene PvdQ is iron-regulated (FUR-repressed), and appears to be involved in pyoverdine biosynthesis, based on evidence from both microarray and mutagenesis studies (18, 29). The effects of the constitutive expression of plasmid-encoded PvdQ in strain PAO1 were examined to gather information on its complicated control mechanism. Remarkably, 3OC12HSL did not accumulate during growth of *P. aeruginosa* constitutively expressing PvdQ in a rich medium, in striking contrast to the behavior of the wild type, which produced micromolar amounts of this quorum signal (FIG. 6).

Two PvdQ knockout mutants grew with 3OC12HSL as a sole energy source, suggesting that another enzyme confers the AHL growth phenotype in strain PAO1. Although some contribution of PvdQ to AHL-utilization cannot be ruled out, it is more likely, as previously suggested, that this protein is involved in an editing reaction during the maturation of the pyoverdine siderophore (18, 29). However, 3OC12HSL also may be subject to inadvertent biochemical degradation by PvdQ during times of pyoverdine expression. The gene encoding the acylase AHL-utilization phenotype of *P. aeruginosa* has not yet been described.

*P. aeruginosa* mutants, in which the PvdQ gene was knocked out, were able to grow in long chain AHL-acylases, as compared to *E. coli* expressing PvdQ, which catalyzed the inactivation of long chain AHLs and the release of HSL. In addition, *P. aeruginosa* engineered to express PvdQ did not accumulate long chain (3OC12HSL) quorum signals. These results confirm that the degradation of AHL acylase was due to increased AHL acylase activity, and indicate that methods for increasing AHL acylase activity can be useful for decreasing virulence by degrading quorum sensing AHLs.

Accordingly, the present invention provides methods of identifying an agent that modulates γ-proteobacterium long chain AHL acylase activity by contacting at least one sample containing the AHL acylase and a long chain AHL with a test agent, under conditions suitable for AHL acylase activity, and detecting a change in AHL acylase activity in the presence of the test agent as compared to the AHL acylase activity in the absence of the test agent, wherein a change in AHL acylase activity identifies the test agent as an agent that modulates the γ-proteobacterium long chain AHL acylase activity. As used herein, the term "modulate" means to increase or decrease. As used herein, the term "long chain AHL" means an AHL having a fatty acid moiety containing eight or more carbon residues (e.g., C8HSL, C10HSL, 3OC12HSL, C14HSL). In comparison, the term "short chain AHL" means an AHL having a fatty acid moiety containing seven or fewer carbon residues (e.g. C4HSL, C6HSL, 3OC6HSL, C7HSL).

An AHL acylase useful in a method of the invention can be any AHL acylase that degrades long chain, but not short chain, AHLs. Generally, the AHL acylase is a γ-proteobacterium AHL acylase, for example, a *Pseudomonas* PvdQ AHL acylase, which has an amino acid sequence as set forth in SEQ ID NO:2 (encoded by SEQ ID NO:1), or a *Pseudomonas* PA1032 AHL acylase, which has an amino acid sequence as set forth in SEQ ID NO:4 (encoded by SEQ ID NO:3) or SEQ ID NO:5 (encoded by nucleotides 19 to 2544 of SEQ ID NO:3; alternative initiator methionine residue at nucleotides 19 to 21 of SEQ ID NO:3). The term "AHL acylase activity" is used herein to refer to the enzymatic activity of an AHL acylase, including the rate of long chain AHL degradation (breakdown) by an AHL acylase. AHL acylase activity can be measured using methods as disclosed herein or methods of determining enzyme kinetics as otherwise known in the art, such that an increase or decrease in AHL activity due to contact with a test agent can be identified. Reference herein to "AHL acylase gene expression" means transcription and translation, or translation, of an AHL acylase coding sequence such that the AHL acylase protein is produced. Increased AHL acylase gene expression results in increased AHL acylase levels produced by a γ-proteobacterium, and decreased AHL acylase gene expression results in decreased AHL acylase levels produced by a γ-proteobacterium. An agent that increases AHL acylase gene expression, for example, can act by inducing transcription of a γ-proteobacterium AHL acylase gene or by derepressing the γ-proteobacterium AHL acylase gene, or increasing translation of an AHL acylase coding sequence (e.g., mRNA). In this respect, it should be recognized that iron starvation has been reported to up-regulate the locus comprising AHL acylase gene, PvdQ, in *Pseudomonas*, and that a "late" response is observed in *Pseudomonas* following contact with 3OC12HSL, suggesting 3OC12HSL directly or indirectly induces AHL acylase gene expression; these aspects of AHL acylase gene regulation are not considered to be encompassed within the present methods.

The methods of the invention provide screening assays useful for determining whether a test agent can modulate the activity of a γ-proteobacterium AHL acylase. As used herein, the term "test agent" means any compound that is being examined for the ability to modulate AHL acylase activity. A test agent (and an agent that modulates AHL acylase activity identified by a method of the invention) can be any type of molecule, including, for example a peptide, a polynucleotide, an antibody, a glycoprotein, a carbohydrate, a small organic molecule, or a peptidomimetic.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be an isolated naturally occurring polynucleotide or portion thereof or a synthetic polynucleotide, and can be single stranded or double stranded, as well as a DNA/RNA hybrid. A polynucleotide agent (or test agent) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994; Ecker and Crooke, *BioTechnology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Peptides also can be useful as test agents. The term "peptide" is used broadly herein to refer to a molecule containing two or more amino acids or amino acid analogs (or modified forms thereof) linked by peptide bonds. As such, peptide test agents (or agents) can contain one or more D-amino acids and/or L-amino acids; and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment. Further, the stability of a peptide agent (or test agent) can be improved by generating (or linking) a fusion protein comprising the peptide and a second polypeptide (e.g., an Fc domain of an antibody) that increases the half-life of the peptide agent in vivo. Peptides also can be modified to have decreased stability in a biological environment, if desired, such that the period of time the peptide is active in the environment is reduced.

Antibodies provide an example of peptides useful as test agents in a screening assay of the invention. As used herein, the term "antibody" is used in its broadest sense to include polyclonal and monoclonal antibodies, as well as antigen binding fragments of such antibodies. Antibodies are characterized, in part, in that they specifically bind to an antigen, particularly to one or more epitopes of an antigen. The term "binds specifically" or "specific binding activity" or the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $1 \times 10^{-9}$ M or $1 \times 10^{-10}$ M or less. As such, Fab, $F(ab')_2$, Fd and Fv fragments of an antibody that retain specific binding activity are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1999); Hilyard et al., *Protein Engineering: A practical approach* (IRL Press 1992); Borrabeck, *Antibody Engineering*, 2d ed. (Oxford University Press 1995); each of which is incorporated herein by reference)

A screening assay of the invention is practiced by contacting a sample that contains (or to which can be added) an AHL acylase and/or a long chain AHL, under conditions suitable for AHL acylase activity. Such conditions are exemplified herein (see Examples 1 and 2), and include, for example, an appropriate concentration of iron ions sufficient for AHL acylase activity, as well as appropriate buffer conditions (including pH), salt concentration (e.g., physiological), and other conditions, which can be selected based on whether the assay is performed in a cell free format or is performed in a cell based assay.

As disclosed herein, a screening assay of the invention can be performed in vitro (e.g., in a cell free system using purified or partially purified components) or in a cell (e.g., in a cell or tissue culture system). Where the method is performed in vitro, the AHL acylase can be a purified naturally occurring AHL acylase, which can be obtained, for example, from an extract comprising a *Pseudomonas* species (e.g., *P. aeruginosa*), or can be a synthetic AHL acylase prepared, for example, using an in vitro translation or coupled transcription/translation reaction using a polynucleotide as set forth in SEQ ID NO:1 or SEQ ID NO:3, including nucleotides 1 to 2544 or nucleotides 19 to 2544 of SEQ ID NO:3, as a template. Where the method is performed as a cell based assay, the sample can be a cell sample, wherein the AHL acylase is expressed in the cell. The cell can be a γ-proteobacterium, in which the AHL acylase is expressed in nature (e.g., a *Pseudomonas* species such as *Pseudomonas aeruginosa*), can be a host cell or tissue sample that is infected with γ-proteobacteria (e.g., a biopsy sample from a subject infected with the bacteria), or can be a cell that has been genetically modified to express a polynucleotide encoding a γ-proteobacterium AHL acylase (e.g., a host cell transformed, transfected or transduced with a polynucleotide encoding the AHL; see Example 2).

Where a test agent is identified as having γ-proteobacterium AHL acylase modulating activity, a screening assay of the invention can further include a step of determining an amount by which the agent increases or decreases γ-proteobacterium AHL acylase modulating activity. For example, where an agent is identified that increases AHL acylase activity in a cell, a method of the invention can further include determining an amount by which the agent increases AHL acylase activity above a basal level. Such an agent can be identified by measuring the amount of AHL acylase activity in a single sample both before adding the test agent and after adding the test agent, or can be identified for example, using two samples, wherein one sample serves as a control (no test agent added) and the other sample includes the test agent. As such, a method of the invention provides a means to obtain agents or panels of agents that variously modulate AHL acylase activity.

A screening assay of the invention also provides a means to determine an amount of a particular agent useful for effecting a desired level of AHL acylase activity. Such a method can be performed by contacting aliquots of a sample with different amounts of the same or different test agents or different amounts of the same or different agents previously identified as having AHL acylase modulating activity. As such, the methods of the invention can be used to confirm that an agent believed to have a particular activity, in fact, has the activity, thus providing a means, for example, to standardize the activity of the agent.

The screening method of the invention is readily adaptable to high throughput format, thus allowing for the screening, in parallel, of one or more test agents using one or more samples, wherein the agents and/or samples independently are the same or different. As such, the method allows for testing one or more concentrations of one or more test agents to identify a concentration of an agent particularly useful for modulating a γ-proteobacterium AHL acylase activity. Further, the method allows for examining several same test agents on one or a plurality of same samples, thus providing a means to obtain statistically significant results. In various aspects, the high throughput format can be used for screening one or a plurality of cell sample(s) taken from a subject having a γ-proteobacterium (e.g., *P. aeruginosa*) infection with one or a plurality of the same (e.g., different concentrations) or different test agents, to identify an agent and/or concentration of agent that is best suited, for example, for increasing AHL acylase activity in the patient, which increases the rate of breakdown of long chain AHLs produced by the γ-proteobacterium, thus providing an agent that reduces or inhibits quorum sensing activity by the infecting bacteria, thereby ameliorating the infection.

When performed in a high throughput (or ultra-high throughput) format, the method can be performed on a solid support (e.g., a microtiter plate, a silicon wafer, or a glass slide), wherein samples to be contacted with a test agent are positioned such that each is delineated from each other (e.g., in wells). Any number of samples (e.g., 96, 1024, 10,000, 100,000, or more) can be examined in parallel using such a method, depending on the particular support used. Where samples are positioned in an array (i.e., a defined pattern), each sample in the array can be defined by its position (e.g., using an x-y axis), thus providing an "address" for each sample. An advantage of using an addressable array format is that the method can be automated, in whole or in part, such that reagents (e.g., test agents) can be dispensed in (or removed from) specified positions at desired times, and samples (or aliquots) can be monitored for AHL acylase activity.

When used in a high throughput format, a method of the invention provides a means to conveniently screen combinatorial libraries of test agents, which can be a library of random test agents, biased test agents (see, for example, U.S. Pat. No. 5,264,563, which is incorporated herein by reference), or variegated test agents (see, for example, U.S. Pat. No. 5,571,698, which is incorporated herein by reference), in order to identify those agents that can modulate γ-proteobacterium AHL acylase activity. Methods for preparing a combinatorial library of molecules that can be screened for AHL acylase modulating activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13 19, 1991; each of which is incorporated herein by reference); a peptide library (U.S. Pat. No. 5,264,563, which is incorporated herein by reference); a library of peptide derivative compounds such as a hydroxamate compound library, reverse hydroxamate compound library, a carboxylate compound library, thiol compound library, a phosphinic peptide library, or phosphonate compound library (see, for example, Dive et al., *Biochem. Soc. Trans.* 28:455-460, 2000; Ye and Marshall, "Peptides: The Wave of the Future" (Lebl and Houghten, ed.; American Peptide Society, 2001), each of which is incorporated herein by reference); a peptidomimetic library (Blondelle et al., *Trends Anal. Chem.* 14:83 92, 1995, which is incorporated herein by reference); a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference); an oligosaccharide library (York et al., *Carb. Res.* 285:99-128, 1996; Liang et al., *Science* 274:1520 1522, 1996; Ding et al., *Adv. Expt. Med. Biol.* 376:261 269, 1995; each of which is incorporated herein by reference); a lipoprotein library (de Kruif et al., *FEBS Lett.* 399:232 236, 1996, which is incorporated herein by reference); a glycoprotein or glycolipid library (Karaoglu et al., *J. Cell Biol.* 130:567 577, 1995, which is incorporated herein by reference); or a chemical library containing, for example, drugs or other pharmaceutical agents (Gordon et al., *J. Med. Chem.* 37:1385-1401, 1994; Ecker and Crooke, *BioTechnology* 13:351-360, 1995; each of which is incorporated herein by reference).

As disclosed herein, a method of the invention can be performed using a sample comprising a cell, tissue or biologic fluid obtained from a subject having a γ-proteobacterium infection (e.g., a subject having a *Pseudomonas* infection). The subject can be any subject susceptible to infection by the γ-proteobacterium, including any vertebrate such as a mammal (e.g., a human subject infected by *P. aeruginosa* or by *V. cholerae*). As such, the methods provide a means to identify an agent that is useful for ameliorating a pathology due to a γ-proteobacteria infection in a subject (e.g., a *Pseudomonas, Vibrio, Legionellales, Azotobacter*, or *Enterobacteriales* infection). As used herein, the term "ameliorate" means that signs and/or symptoms of a γ-proteobacteria infection in a subject are reduced (lessened). Such a method can be performed, for example, by administering to the subject an agent that modulates AHL acylase activity of a γ-proteobacterium by degradation of long chain AHLs, thereby preventing autoinduction which would otherwise occur due to quorum bacteria reaching threshold concentrations. As such, immunocompromised subjects, subjects afflicted with cystic fibrosis, burn patients, and any other subject particularly susceptible to infection by an opportunistic γ-proteobacterium can benefit from treatment with an agent identified according to a method of the invention.

Amelioration of a γ-proteobacteria infection can be identified using any assay generally used to monitor the clinical signs or the symptoms of the particular disorder. For example, *P. aeruginosa* generally infects the lungs and, therefore, the skilled clinician would know that a subject having such an infection can be monitored by testing a sputum sample of the subject for *P. aeruginosa*, wherein decreased amounts or activity of the *P. aeruginosa* are indicative of amelioration. Similarly, the cardinal signs of infection (e.g., fever) generally are observed in such infected subjects and can be monitored using routine and well known methods. In addition, amelioration can be identified by the subject indicating that he or she feels better following treatment with an agent identified according to a method of the invention.

Where the agent is to be used for a therapeutic method, it can be formulated in a form suitable for administration to a subject, for example, as a pill or a liquid, and can be administered, for example, orally, by injection, or via inhalation. Accordingly, compositions, including medicaments, useful for treating a subject infected with a γ-proteobacterium (e.g., *P. aeruginosa*) are provided. A composition for administration to a living subject generally includes formulating the agent in a pharmaceutically acceptable composition. Such compositions are well known in the art and include, for example, aqueous solutions such as water or physiologically buffered saline or other solvents or vehicles such as glycols, glycerol, oils such as olive oil or injectable organic esters. The composition also can contain physiologically acceptable compounds that act, for example, to stabilize or to increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients.

One skilled in the art would know that the choice of a composition, including a physiologically acceptable compound, depends, for example, on the physico-chemical characteristics of the agent to be administered, and on the route of administration of the composition, which can be, for example, orally or parenterally such as intravenously, and by injection, intubation, inhalation, or other such method known in the art. The composition also can contain one or more additional reagents, including, for example, nutrients or vitamins or, where the composition is administered for a therapeutic purpose, a diagnostic reagent or therapeutic agent relevant to the disorder being treated.

The composition can be administered to a subject by any of various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the composition can be administered by injection, intubation, orally or topically, the latter of which can be passive, for example, by direct application of an ointment, or active, for example, using a nasal spray or inhalant, in which case one component of the composition is an appropriate propellant. Inhalation can be a particularly useful means of administration where the γ-proteobacterium infection is in the lungs (e.g., a *P. aeruginosa* infection).

The following examples are intended to illustrate but not limit the invention.

EXAMPLE 1

Isolation and Growth of *Pseudomonas* Strains

This example illustrates how different *Pseudomonas* bacterial strains responded when isolated and given only 3OC12HSL-containing medium as an energy source. The bacterial strains used were: *Pseudomonas* strain PAI-A (isolation described below); *P. aeruginosa* PA14 (obtained from Dianne Newman of Caltech); *P. aeruginosa* PAO1 and QSC112a (obtained from E. Peter Greenberg of the University of Iowa; 43); *P. aeruginosa* PAO1 and an in-frame PvdQ-deletion/GenR$^R$-cassette-replacement mutant of this PAO1 Denver strain (both obtained from Michael Vasil of the University of Colorado Health Sciences Center; 29); *P. aeruginosa* PAO1 containing pPvdQ-Nde (see below), a constitutive PvdQ expression vector derived from pUCP-Nde (4); *E. coli* DH5α carrying pUCP18-Nde (obtained from Ciaran Cronin of the University of California, San Francisco); *E. coli* BL21PRO containing pPvdQ-PROTet, a pPROTet.E133-derived tet-inducible PvdQ expression vector encoding tetracycline and spectinomycin resistance (see below); and *E. coli* BL21RO containing the autonomously replicating plasmid, pPROTet.E133 (Clontech).

Media and growth conditions. LB, amended with antibiotics when appropriate, was used for growth and maintenance of all strains unless otherwise stated. For the 3OC12HSL-dependent enrichment of strain PAI-A and other growth experiments performed on this strain, modified "MES 5.5" defined-medium was used to enrich and study *Variovorax paradoxus* VAI-C (21). These modifications to the medium included buffering with 5 mM 3-(N-morpholino)-propanesulfonic acid (MOPS) at pH 7.2 and the addition of sodium sulfate (14 g·liter$^{-1}$) and magnesium chloride (4 g·liter$^{-1}$). For growth experiments with *P. aeruginosa*, "MES 5.5" defined medium was used as described previously (21) with the exception that it contained sodium sulfate, not sulfite, as S-source, a typographical error in the reported recipe. Unless otherwise noted, the medium was buffered to a pH of 5.5 with 5 mM 2-(N-morpholino)-ethanesulfonic acid (MES). Ammonium-free "MES 5.5" basal medium was used to examine the utilization of AHLs and HSL as potential nitrogen sources. 100 mM stock solutions of AHLs were prepared by dissolving AHLs in ethyl acetate that had been acidified with glacial acetic acid (0.01% v/v), and stocks were stored at −20° C. AHLs used in these studies were: N-3-oxododecanoyl-L-homoserine lactone (3OC12HSL; Quorum Sciences Inc., Iowa City Iowa), N-3-oxohexanoyl-L-homoserine lactone (3OC6HSL; Sigma), and from Fluka: N-3-butanoyl-DL-homoserine lactone (C4HSL), N-3-hexanoyl-DL-homoserine lactone (C6HSL), N-3-heptanoyl-DL-homoserine lactone (C7HSL), N-3-octanoyl-DL-homoserine lactone (C8HSL), N-3-dodecanoyl-DL-homoserine lactone (C10HSL), N-3-dodecanoyl-DL-homoserine lactone (C12HSL), N-3-tetradecanoyl-DL-homoserine lactone (C14HSL). For growth experiments, the AHL was dispensed into sterile tubes, the ethyl acetate was removed by evaporation under a stream of sterile air, and sterile medium was added to the dried AHL that remained. Stocks of L-HSL (Sigma) were prepared just prior to their use from well-desiccated reagent stored at −20° C. That homoserine contamination was not present was verified via thin layer chromatography and ninhydrin staining (16). Cells were grown in 5 ml of medium in 18-mm tubes with shaking at 37° C. unless otherwise noted. AHL molecules are stable for approximately 30 days under the conditions of low pH in our defined medium (9, 34). Unless noted, all other reagents were of reagent grade.

Enrichment and isolation procedures. Turf soil was collected in May of 2000 at the University of Iowa. The soil was disrupted and dispersed with a metal spatula, and remaining large particles were removed. One hundred milligrams of the soil were added to 5 ml of the vitamins replete, ammonium-replete enrichment medium containing 1 mM 3OC12HSL as a sole energy source (see above). After 2 days of incubation with shaking at 37° C., a 1% (vol/vol) transfer was made into like medium. This culture was incubated without agitation at room temperature for 3 months after which the culture was transferred once more into 3OC12HSL-containing medium before being streaked for isolation on rich media. Because 3OC12HSL is not soluble at the concentrations employed for growth, isolation was on LB agar with subsequent verification of the AHL-degradation phenotype in the defined liquid medium.

Growth studies. Optical density measurements were performed at 600 nm using a Spectronic 20 spectrophotometer. AHLs with side chains of greater than 6 carbons in length were poorly soluble, so the ethyl acetate carrier was evaporated in the glass tube such that a uniform coating of AHL was beneath the spectrophotometer's light path. When care was taken to vortex tubes gently, the changes in optical density reflecting growth could be monitored accurately. Molar growth yields were determined in the defined media containing the indicated substrate at a final concentration of 1 or 2 mM. For both *Pseudomonas* PAI-A and *P. aeruginosa* PAO1, factors for converting optical density to cell dry mass were determined by growing cells in media containing succinate as the energy source and $NH_4Cl$ as the nitrogen source, washing the cells with 50 mM ammonium acetate buffer (pH 5.5), and drying cell samples to a constant weight. Such determinations were made in quadruplicate.

Enrichment and isolation of a bacterium that utilizes 3-oxododecanoyl-HSL as a sole energy source. An enrichment culture using a 3OC12HSL-containing minerals and vitamins medium became turbid within 48 hours after inoculation with turf soil. No growth was evident in a control lacking energy nutrient. The cells were rods of uniform morphology and were well dispersed in the medium. They did not form clumps, a pellicle, or attach to the glass at the air-medium interface. When the culture was streaked on LB agar medium for isolation, a single, uniform colony morphotype was observed. Pure cultures were obtained after several successive streaks from single colony picks. Growth of a representative isolate, designated strain PAI-A, was confirmed in the 3OC12HSL-containing liquid medium.

Examination of *Pseudomonas aeruginosa* strains for the ability to utilize 3OC12HSL. Two clinical strains of *P. aeruginosa*, PAO1 and PA14, were examined for the ability to utilize 3OC12HSL in defined, ammonia-replete media at both pH 5.5 and 7.2. Both strains grew rapidly at both pHs using succinate as a sole energy source. Although initially it appeared as if neither would utilize the quorum signal as an energy nutrient, the strains began to grow exponentially with a doubling time ranging from 11-25 days after several weeks incubation. The length of the initial lag phase in cultures inoculated using naive cells (those not previously grown on AHL) was highly variable, ranging from 10 to 30 days. Curiously, AHL-grown cells that were transferred directly into AHL-containing media did not show significant lags in growth, but those transferred and grown in media containing a different energy substrate followed by re-introduction into AHL both re-exhibited long lag phases. The issues underlying the long lags exhibited by naive cells and their subsequent adaptation to growth on AHLs have not been further clarified.

*Pseudomonas* PAI-A and *P. aeruginosa* PAO1 degrade and utilize long acyl AHLs. Strains PAI-A and PAO1 grew on a number of AHLs, but no growth was observed with AHLs with acyl side chains shorter than 8 carbons (Table 1). When provided with 1 mM C4HSL as a co-substrate in 3OC12HSL-containing media, PAI-A and PAO-1 did not degrade detectable amounts of the short chain AHL or exhibit any C4HSL-dependent stimulation of their growth yields. Optical density to "dry weight biomass" conversion factors were determined to be, at an $OD_{600}$ of $1.0: 346 \pm 7$ $\mu g \cdot ml^{-1}$ for strain PAO-1, and $337 \pm 8$ $\mu g \cdot ml^{-1}$ for strain PAI-A. The doubling times of strains PAI-A and PAO1 were comparable for many substrates (Table 1). *P. aeruginosa* PAO1 utilized both the D-forms and L-forms of AHLs, as determined by substrate disappearance and comparison of the molar yields on L-forms and DL-forms. Curiously, no increase in molar growth yield was observed as a function of AHL acyl lengths, i.e. when comparing growth on C10HSL, C12HSL, and C14HSL (for contrast, see FIG. 5 of (21)). The AHL molar growth yields for strain (str.) PAO-1 were only 49% to 67% of that achieved during its growth on the corresponding fatty acids (Table 1). Growth on fatty acids revealed the expected, incremental increase in molar yield as a function of increased acyl length. Neither strain PAI-A nor PAO1 used HSL as sole or supplementary energy source.

TABLE 1

Growth of *P. aeruginosa* PAO1 and *Pseudomonas* strain PAI-A on acyl-homoserine lactones and other energy sources[a]

| | *P. aeruginosa* PAO1 | | *Pseudomonas* Strain PAI-A | |
|---|---|---|---|---|
| Substrate | Yield (g · mol$^{-1}$) | Doubling time (h) | Yield (g · mol$^{-1}$) | Doubling time (h) |
| C8-DL-HSL | 95 ± 4 | 15.0 ± 2 | +, ND[b] | ND |
| C10-DL-HSL | 97 ± 3 | 14.0 ± 3.8 | +, ND | ND |
| 3OC12-L-HSL | 76 ± 10 | 25.0 ± 3 | 84 ± .2 | 25.0 ± 3.5 |
| C12-DL-HSL | 84 ± 7 | 14.9 ± 7.5 | 80 ± 18 | 16.5 ± 3 |
| C14-DL-HSL | 84 ± 12 | 21.0 ± 5.3 | +, ND | ND |
| Succinate | 43 ± 3 | 0.6 ± .09 | 49 ± 3.8 | 0.6 ± .02 |
| Decanoate | 130 ± 3 | ND | 126 ± .5 | ND |
| Dodecanoate | 141 ± 4 | ND | 155 ± 8.4 | ND |
| Tetradecanoate | 177 ± 16 | ND | 198 ± 3 | ND |

[a] Values represent the averages ± standard errors from at least duplicate cultures. Studies were performed with minimal salts media buffered at pH 5.5 for strain PAO1 and pH 7.2 for strain PAI-A. Neither strain utilized HSL, homoserine, C4HSL, 3OC6HSL, C6HSL, or C7HSL as an energy source.
[b] +, positive yield; ND, not determined.

Strains PAI-A and PAO1 release HSL as an initial product of AHL degradation. Thin layer chromatography of clarified reaction fluids, harvested from dense cell suspensions of strains PAI-A and PAO1 incubated with 25 mM C12HSL, revealed the AHL-dependent release of ninhydrin-reactive materials. These had the same yellow and purple staining characteristics and migration characteristics as authentic HSL and homoserine, respectively (data not presented). In contrast, cell-free, AHL-free, and cell and AHL-free controls did not produce ninhydrin reactive materials after similar incubation periods. The TLC data suggests that both strains catalyze the initial step of AHL degradation via an HSL-releasing acylase. Because analyses of biological AHL degradations are less ambiguous at pH 5.5 than they are at pH 7.2, and because strain PAI-A does not grow on AHLs at pH 5.5, P. aeruginosa was chosen for further experiments.

Figure 3A:
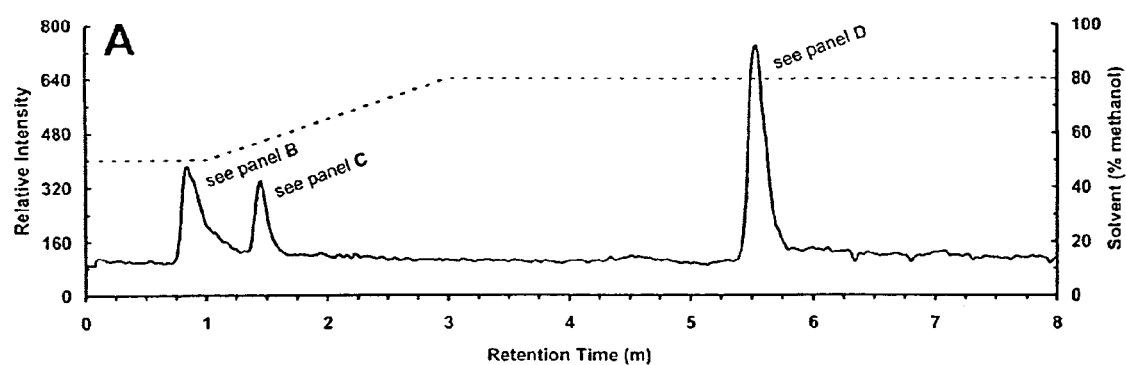
Figure 3A:
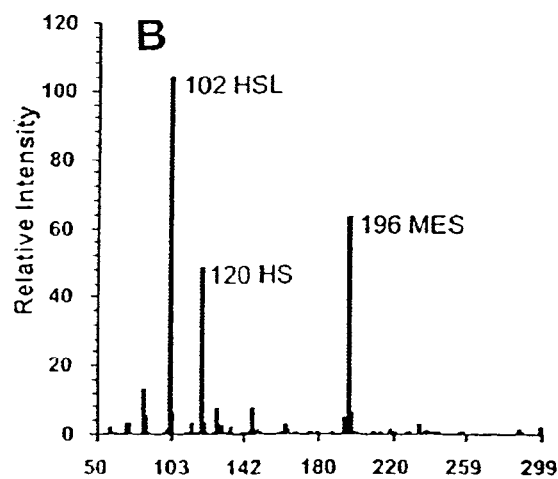
Figure 3B:
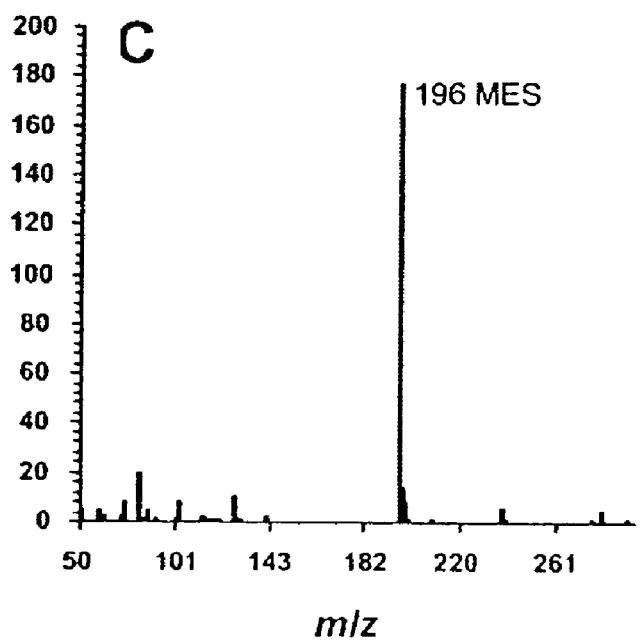
Figure 3B:
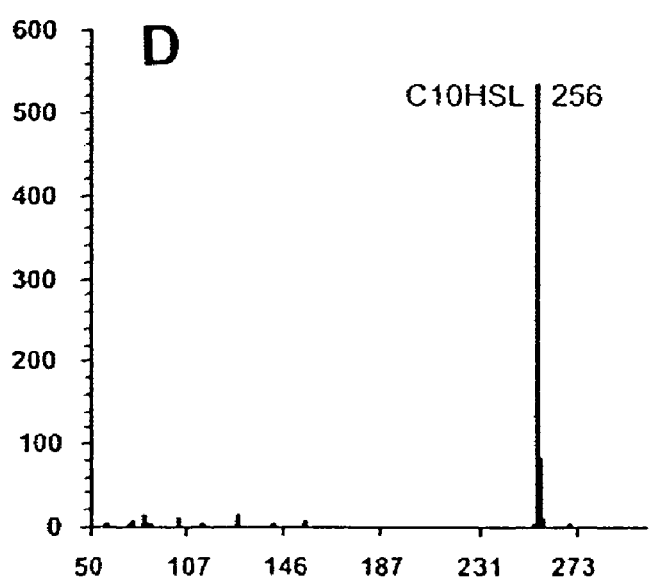

APCI LC/MS analyses confirmed that P. aeruginosa PAO1 releases HSL and homoserine as AHL degradation products. A representative chromatogram of cell-free fluid from a C10HSL-grown culture is shown in FIG. 3A. Although HSL and HS elute at similar times, both compounds were resolved by extracting the M+1 molecular ions 102 and 120, respectively, from the raw chromatogram (a standard MS practice).

Figure 4:
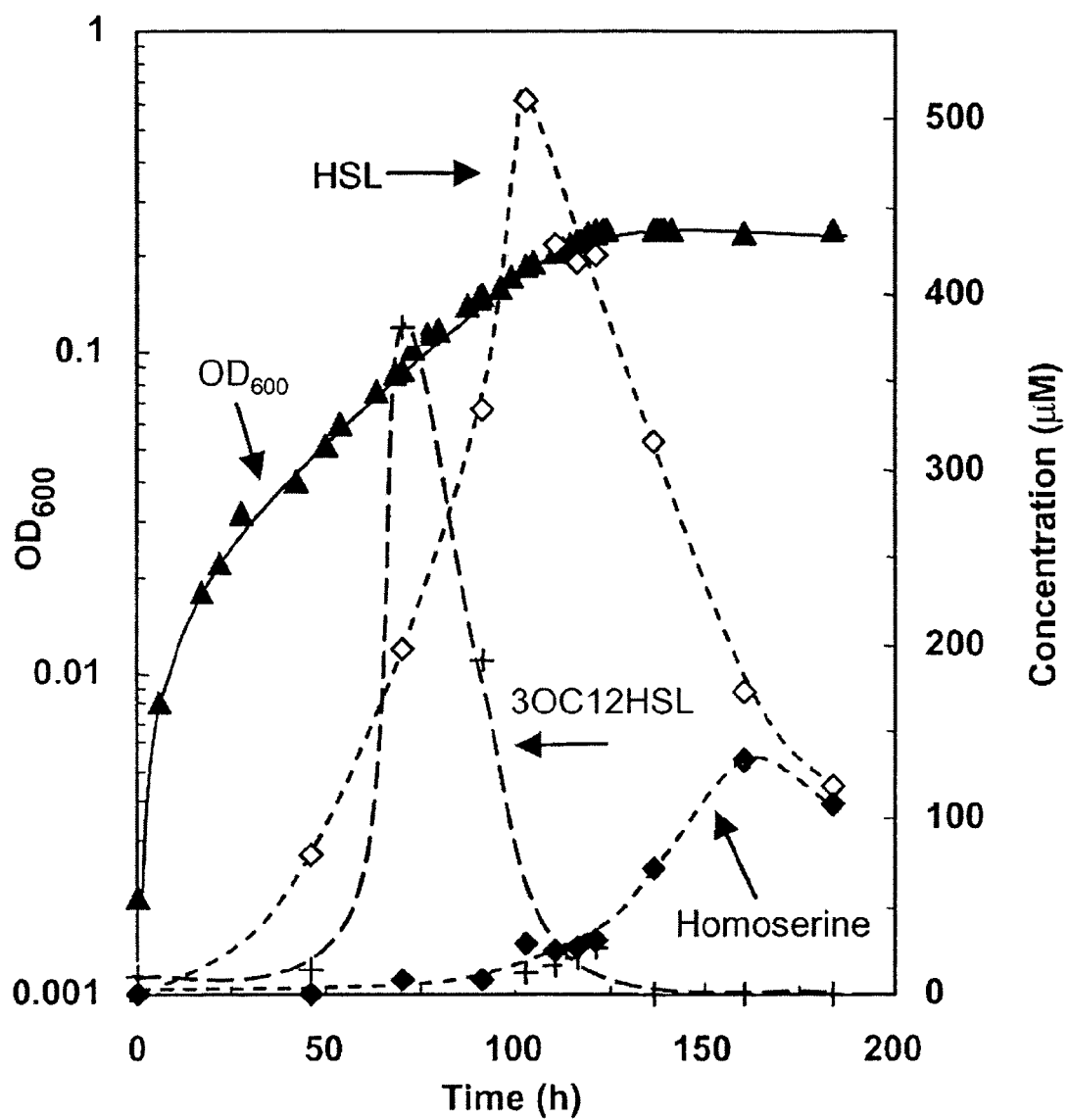
FIG. 4 shows growth of $P.$ aeruginosa PAO1 in ammonia-replete MES 5.5 media containing 1 mM 3OC12HSL as the sole energy source. Substrate consumption and product accumulation were determined via LC/APCI-MS. Note that since the 3OC12HSL substrate was poorly soluble at the initial concentrations employed; virtually no AHL was observed in the culture fluid at the time of inoculation. As growth progressed, a transient spike of AHL in solution was observed. HSL accumulated throughout the growth phase but was degraded upon entry into stationary phase yielding a transient intermediate, homoserine. 3OC12-homoserine concentrations remained static throughout the course of the experiment and never exceeded 0.1% of the initial AHL concentration. Culture pH was well controlled throughout the study.

P. aeruginosa PAO1 growth and metabolism of 3OC12HSL as the sole energy source in "MES 5.5" medium is shown in FIG. 4. By early stationary phase, all of the white, nearly insoluble 3OC12HSL-substrate was consumed such that concentrations of less than 125 nM remained. HSL accumulated throughout the growth phase and reached a maximum of ca. 500 µM just before the onset of stationary phase, after which it decreased to less than 80 µM by 100 hours into stationary phase. Concomitant with the disappearance of HSL, the amino acid homoserine accumulated and then decreased to concentrations below 80 µM by 100 hours into stationary phase (FIG. 4). Since the culture pH was well-controlled at pH 5.5, and since the half life decay of HSL into homoserine at this pH is on the order of weeks, an enzymatic HSL lactonase, not abiotic alkaline hydrolysis, is most likely responsible for the evolution of homoserine. P. aeruginosa did not grow using either HSL or homoserine as a sole energy source in "MES 5.5" media. When provided with long chain AHLs as sole sources of carbon and nitrogen, strain PAO1 grew at rates about twice as slowly as cultures utilizing AHL plus ammonium (not shown). Cells did not use either homoserine or HSL as sole sources of energy or nitrogen.

Other Analyses. Strain PAI-A was examined for several traits exhibited by P. aeruginosa, which was used as a positive control. Fluorescent pigment production was examined using Wood lamp illumination of colonies grown on LB agar. Pyocyanin production was examined in glycerol-alanine medium (11). Production of acyl-HSLs in both LB and defined media was examined using previously described radioassay methods (33). A Beckman System Gold HPLC running a methanol gradient was used in the chromatographic analysis of ethyl acetate extracts as previously described (34). Radioactivity was monitored via on-line, solid scintillation counting using an in-line HPLC β-particle detector (IN/US Model 3, Tampa, Fla.). Microscopic examinations were performed using a Zeiss Stemmi 2000 stereomicroscope (low-magnification), and a Zeiss Axioplan research microscope (higher magnification, phase-contrast and dark-field). Nitrate-dependent anaerobic growth was tested using both MOPS-buffered defined media or LB amended to contain 10 mM potassium nitrate dispensed under a 100% $N_2$ headspace in Bellco (Vineland, N.J.) 18-mm butyl, serum-stoppered "Balch" tubes.

Analysis of cell-free culture and reaction fluids. For the initial characterization of the intermediates in AHL degradation, a TLC method was used (16). For a refined analysis, a liquid chromatography-atmospheric pressure chemical ionization mass spectrometry (LC/APCI-MS) technique was developed to monitor and quantify the disappearance of AHL and appearance of a number of AHL degradation products. For this analysis, 50 µl samples of culture fluids were taken in triplicate from AHL-grown cultures and were centrifuged at 15,800×g for 10 minutes. The cell-free culture fluids were stored at −20° C. until all samples had been collected for analysis. For LC/MS analysis, samples were mixed 1:1 with acetic acid-acidified methanol (1% vol/vol). Dilutions were made using "MES 5.5" medium. A C18 ultra aqueous reverse phase column (5 µm bead size, 50 mm×3.2 mm; Restek No. 317553) was employed. The initial mobile phase was 50:50:1 methanol:water:acetic acid running at 0.5 ml min$^{-1}$ isocratically over the first minute after injection and increased (via a linear gradient) to 80:20:1 methanol water:acetic acid over the following 2 minutes (FIG. 3). Using this method, a diversity of AHLs, their corresponding acyl-homoserines, HSL, and homoserine in samples could be quantified from cultures growing in the "MES 5.5" defined medium. These analyses were performed at Caltech's Environmental Analysis Center using a Hewlett Packard 1100 Series LC/APCI-MS mass spectrometer.

Standards over a range of concentrations (125 nM to 1 mM) were prepared using either water or "MES 5.5" basal media depending on the origin of the sample, and were diluted 1 to 1 with acetic acid acidified methanol (1% vol/vol). For a 20 µl sample injection, the detection limits for standards prepared in "MES 5.5" media were: 2.5 pmoles for 3OC12HSL and its corresponding acyl-homoserine, 10 pmoles for C10HSL and its corresponding acyl-homoserine, and 100 pmoles for HSL. The limit of detection for standards prepared in water was lower than for those prepared in medium, but the former but were only used to quantify AHLs recovered from evaporated ethyl acetate extracts. Ethyl acetate extraction did not recover HSL or homoserine. The accurate quantization of homoserine in standards and samples was complicated by its partial lactonization into HSL, a chemical reaction that occurred after injection into the LC/APCI-MS instrument. Thus, while homoserine plus HSL pool sizes could accurately be quantified, homoserine itself was determined with less precision using the LC/APCI-MS method and was usually a slight underestimate.

Figure 2:
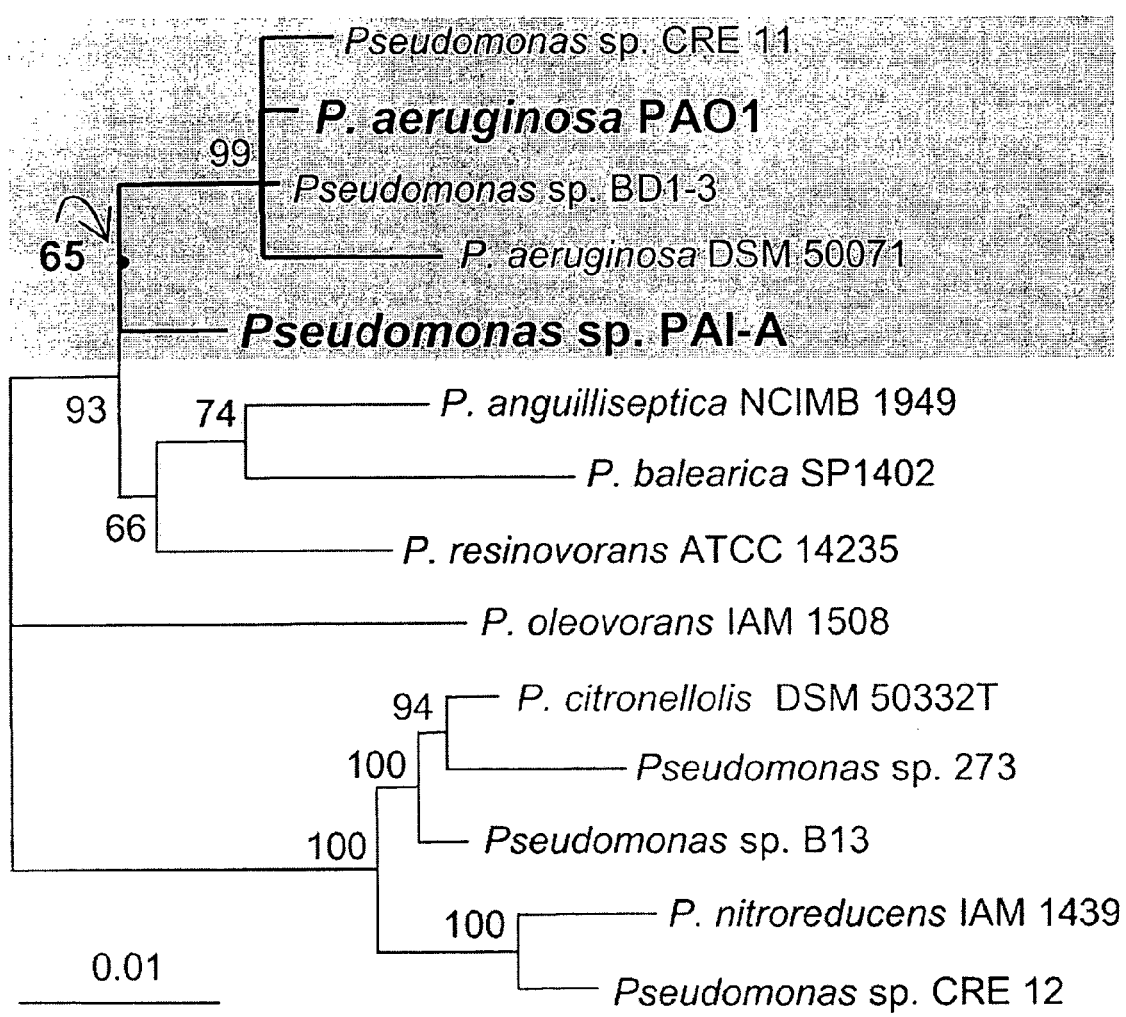
FIG. 2 shows rRNA-based phylogeny of strain PAI-A. Construction of the phylogram used 1,120 unambiguously aligned nucleotide positions in a 10,000-step Tree Puzzle 5.0 maximum-likelihood analysis (36, 39; see Example 1 for GenBank Acc. Nos.). The bar represents evolutionary distance as 0.01 changes per nucleotide position, determined by measuring the lengths of the horizontal lines connecting the species. The numbers provide support for the robustness of the adjacent nodes. The arrow points to the short node from which the five strains within the shaded box radiate.

Nucleotide sequence analysis of the SSU rDNA Strain PAI-A. The nucleotide sequence of a PCR-amplified fragment of the 16S rDNA of strain PAI-A was determined and analyzed using previously described procedures (20, 21). Sequence reads were assembled and edited using Sequencher (Genecodes, Ann Arbor). Multiple sequence alignments, translations, and phylogenetic analyses were performed using the Linux ARB freeware package (www.arb-home.de/). Phylograms were constructed via Puzzle-Map 5.0 maximum likelihood analyses (36). Tree layout was performed using Treeview 1.6.6 for Windows (30). The 1401 base pair sequence for strain PAI-A has been submitted to GenBank (AY288072). The GenBank accession numbers for the other sequences presented in FIG. 2 are as follows: Pseudomonas strain CRE 11, U37338 (28); P. aeruginosa PAO1, AE004949 (38); Pseudomonas strain BD1-3, AB015516; P. anquilliseptica, X99540 (5); P. balearica U26418 (3); P. resinovorans, AB021373 (1); P. oleovorans, D84018 (2); P. citronellolis, Z76659 (26); Pseudomonas strain 273, AF039488 (44); Pseudomonas strain B13, AJ272544 (24); *P. nitroreducens*, D84021 (2); and *Pseudomonas* strain CRE 12, U37339 (28).

Phylogenetic analysis of strain PAI-A. A nearly complete sequence of the SSU rDNA was obtained. Web-based similarity searches against rDNA in the RDP-II and GenBank databases suggested that strain PAI-A was most closely related to *P. aeruginosa* and several other pseudomonads. The small subunit (SSU) rDNA shared 98.4% and 98.1% sequence identity with *P. aeruginosa* PAO1 and *P. resinovorans*, respectively. By any of the distance, parsimony and maximum likelihood methods employed (FIG. 2), the SSU rDNA from str. PAI-A clustered most closely with those from *P. aeruginosa* and its close relatives.

Properties of *Pseudomonas* PAI-A. Strain PAI-A grew aerobically in both defined media and LB at 30° and 37°, but not at 42° C. Cultures doubled every 35 minutes in defined medium with succinate as the sole carbon source at 37° C. The isolate grew on a number of tested substrates at both pH 7.2 and pH 5.5; however, cultures did not grow in AHL-containing media at the latter pH. Cells did not grow anaerobically in either succinate-defined or LB media amended with nitrate. Exponentially growing cells sampled from AHL-containing media were vigorously motile rods, 2.5×0.8 pm in dimension. The isolate formed creamy-white colonies with spreading edges. After several days, colonies become smooth, non-sticky, leathery, and extremely recalcitrant to disruption with an inoculating loop.

Strain PAI-A did not produce colored or fluorescent pigments in or on LB or glycerol-alanine (pyocyanin-production) media. Cultures did have any aroma of note. Cells did not grow in media containing 30 μg nalidixate·ml$^{-1}$. To examine *Pseudomonas* PAI-A for the production of AHL quorum signals, cultures grown in both defined and LB media were incubated with $^{14}$C-carboxyl methionine. Since no radioactive peaks were evident after chromatography of the ethyl acetate extract fraction, this isolate does not appear to accumulate AHLs under the conditions examined.

EXAMPLE 2

Characterization of *Pseudomonas* AHL Acylase Activity

Cloning and expression of pvdQ (PA2385) encoding a putative *P. aeruginosa* AHL acylase. Genomic DNA was isolated from *P. aeruginosa* PAO1 using the DNeasy™ tissue kit (QIAGEN) and used as a template for PCR. The deduced coding region for PvdQ (Gene PA2385; www.pseudomonas.com) was amplified from the genomic DNA using the following primers: 5'-AGGCCAAGCT-TATGGGGGATGCGTACCGTACTG-3' (SEQ ID NO:6) and 5'-GTTATATAGCGGCCGCTAGGCATTGCT-TATCATTCG-3' (SEQ ID NO:7; bold print indicates HindIII and NotI restriction sites, respectively), cloned into the appropriately digested expression vector, pPROTet.E133 (Clontech), and transformed into *E. coli* BL21PRO. Recombinant AHL acylase activity was examined as follows. After growth in LB medium containing spectinomycin (50 μg ml$^{-1}$) and chloramphenicol (34 μg ml$^{-1}$), and after gene induction by the addition of anhydrotetracycline (aTc, 100 ng ml$^{-1}$) at 18° C., cells were pelleted and resuspended to a final optical density of 1.2 in MOPS buffered media (pH 7.2) containing 10 μM 3OC12HSL. Recombinant cells that had not been induced with aTc were used as a negative control. Reaction mixtures were incubated at 18° C.; 150 μl samples were removed at 0, 15, 30, and 60 min and analyzed for AHL disappearance and product appearance via LC/APCI-MS (see above).

Constitutive overexpression of PvdQ in *P. aeruginosa*. For the constitutive expression of PvdQ in strain PAO1, the coding sequence was PCR-amplified with the following primers: 5'-AAGAGGACATATGGGGGATGCGTACCG-TACTG-3' (SEQ ID NO:8) and 5'-CTAAAGCTTGGCT-GTGGGCCGCCTCTATGG-3' (SEQ ID NO:9; bold print indicates NdeI and HindIII restriction sites, respectively). The PCR product was cloned into the *E. coli-Pseudomonas* shuttle expression vector pUCP-Nde digested with NdeI and HindIII (4). The resulting construct, pPvdQ-Nde, was transformed into *P. aeruginosa* PAO1 via electroporation. Since the repression of gene expression from this vector requires LacI, and since wild-type *P. aeruginosa* PAO1 does not encode this repressor, the probable acylase was expected to be constitutively expressed, a prediction borne out after the examination of total cell proteins via PAGE.

Analysis and expression of *P. aeruginosa* PvdQ, which encodes a candidate AHL acylase. The *P. aeruginosa* gene PA2385 (recently named PvdQ (18)), which was identified as a close homologue to a gene encoding an HSL-releasing AHL acylase from *Ralstonia* XJ12B (23), was examined to determine whether it encoded a protein with AHL acylase activity and conferred the AHL-dependent growth of *P. aeruginosa*. The coding region of this gene was amplified from the genomic DNA, cloned into an expression vector, and expressed in *E. coli*. The polypeptide encoded by the gene was predicted to be postranslationally cleaved into two distinct subunits. PAGE analysis of the total proteins fraction from *E. coli* cells expressing recombinant PvdQ revealed small amounts of the two expected subunits. The majority of the recombinant protein was recovered as the unprocessed 80 kDa propeptide. This observation is similar to that noted by Zhang and co-workers for recombinant AiiD, the *Ralstonia* AHL acylase (23).

Resting cell suspensions expressing PvdQ were incubated with 10 μM 3OC12HSL, which is a concentration relevant to the quorum sensing physiology of *P. aeruginosa*. AHL disappearance and the appearance of HSL and 3OC12-homoserine were evaluated using the LC/APCI-MS analysis of cleared reaction fluids (FIG. 5). Within an hour, the AHL disappeared concurrent with the accumulation of stoichiometric amounts of HSL as product. No 3OC12-homoserine accumulation was observed. Cell-free and uninduced cell controls did not catalyze HSL release or the degradation of the AHL over the same time period. In a pattern similar to the AHL utilization data (Table 1), cells of *E. coli* expressing the recombinant acylase catalyzed the HSL-releasing degradation of C14HSL, C12HSL, C10HSL. and C8HSL, but not 3OC6HSL or C6HSL. The effects of the constitutive expression of PvdQ in *P. aeruginosa* PAO1 were also examined. In comparison to wild-type, which accumulated 3OC12HSL to concentrations in excess of 6 μM during growth in LB at 30° C. (FIG. 6), cultures expressing the acylase did not accumulate any of this quorum signal above the threshold of detection.

A PvdQ deletion-replacement mutant and the strain QSC112a, which carries a Tn5-insertion into PvdQ, were also examined for growth in defined media with 3OC12HSL as sole energy source. Both mutants grew with the same growth rates and yields as wild-type (data not presented). Accumulations of endogenously produced 3OC12HSL by LB-grown cultures of the PvdQ-deletion mutant were identical to that of the wild-type grown under the same conditions. Evidently, although PvdQ encodes an enzyme with an HSL releasing AHL acylase activity specific towards long-chain AHLs, another enzyme must be a significant contributor to the growth phenotype on AHL.

Each of the following publications is incorporated herein by reference.
1. Anzai et al., 2000. *Int J Syst Evol Microbiol* 50:1563-89.
2. Anzai et al., 1997. *Int J Syst Bacteriol* 47:249-51.
3. Bennasar et al., 1996. *Int J Syst Bacteriol* 46:200-5.
4. Cronin and McIntire, 1999. *Anal Biochem* 272:112-115.
5. Domenech Fernandez-Garayzabal et al., 1997. *Aquaculture* 156:317-326.
6. Dong et al., 2002. *Appl Environ Microbiol* 68:1754-9.
7. Dong et al., 2001. *Nature* 411:813-817.
8. Dong et al., 2000. *Proc Nat Acad Sci USA* 97:3526-31.
9. see Schaefer et al., 2000. *Method Enzymol* 305:288-301.
10. Flagan et al., 2003. *Appl Environ Microbiol* 69:909-916.
11. Frank and DeMoss, 1959. *J Bacteriol* 77:776-782.
12. Fuqua et al., 2001. *Ann. Rev Genet* 35:439-68.
13. Hanzelka et al., 1999. *J Bacteriol* 181:5766-5770.
14. Jakubowski, 1997. *Biochemistry* 36:11077-85.
15. Jakubowski, 2000. *J Biol Chem* 275:3957-62.
16. Jakubowski, 1995. *J Biol Chem* 270:17672-3.
17. Kobayashi et al., 1998. *Proc Natl Acad Sci USA* 95:12787-12792.
18. Lamont and Martin, 2003. *Microbiology* 149:833-42.
19. Leadbetter, 2001. *Nature* 411:748-749.
20. Leadbetter and Breznak, 1996. *Appl Environ Microbiol* 62:3620-3631.
21. Leadbetter and Creenberg, 2000. *J Bacteriol* 182:6921-6.
22. Lee et al., 2002. *Appl Environ Microbiol* 68:3919-24.
23. Lin et al., 2003. *Mol Microbiol* 47:849-860.
24. Mikkat et al., 2000. *Syst Appl Microbiol* 23:31-40.
25. Miller and Bassler, 2001. *Ann. Rev Microbiol* 55: 165-99.
26. Moore et al., 1996. *Syst Appl Microbiol* 19:478-492.
27. Moré et al., 1996. *Science* 272:1655-1658.
28. Mueller et al., 1997. *Antonie Van Leeuwenhoek* 71:329-43.
29. Ochsner et al., 2002. *Mol Microbiol* 45:1277-87.
30. Page, 1996. *Comput Appl Biosci* 12:357-358.
31. Parsek et al., 1999. *Proc Natl Acad Sci USA* 96:4360-4365.
32. Reimmann et al., 2002. *Microbiology* 148:923-32.
33. Schaefer et al., 2001. *Methods Enzymol* 336:41-7.
34. Schaefer et al., 2000. *Method Enzymol* 305:288-301.
35. Schaefer et al., 1996. *Proc Natl Acad Sci USA* 93:9505-9509.
36. Schmidt et al., 2002. *Bioinformatics* 18:502-4.
37. Schuster et al., 2003. *J Bacteriol* 185:2066-79.
38. Stover et al., 2000. *Nature* 406:959-64.
39. Strimmer et al., 1996. *Mol Biol Evol* 13:964-969.
40. Van Delden and Iglewski, 1998. *Emerg Infect Dis* 4:551-60.
41. Voelkert and Grant, 1970. *Anal Biochem* 34:131-137.
42. Wagner et al., 2003. *J Bacteriol* 185:2080-95.
43. Whiteley et al., 1999. *Proc Natl Acad Sci USA* 96:13904-13909.
44. Wischnak et al., 1998. *Appl Environ Microbiol* 64:3507-11.
45. Zakataeva et al., 1999. *FEBS Lett* 452:228-232.
46. Zhang et al., 2002. *Proc Natl Acad Sci USA* 99:4638-4643.

Although the invention has been described with reference to the above examples, it will be understood that modifications and variations are encompassed within the spirit and scope of the invention. Accordingly, the invention is limited only by the following claims.

What is claimed is:

1. A method of identifying an agent that modulates γ-proteobacterium long chain acyl homoserine lactone (AHL) acylase activity, comprising:
   a) contacting at least one sample comprising PA1032 AHL acylase as set forth in SEQ ID NO:4 and a long chain AHL with at least one test agent, under conditions suitable for AHL acylase activity; and
   b) detecting a change in AHL acylase activity in the presence of the test agent as compared to the AHL acylase activity in the absence of the test agent;
   wherein a change in AHL acylase activity identifies the test agent as an agent that modulates the γ-proteobacterium long chain AHL acylase activity.

2. The method of claim 1, wherein the long chain AHL comprises
   N-3-octanoyl-DL-homoserine lactone (C8HSL);
   N-3-decanoyl-DL-homoserine lactone (C10HSL);
   N-3-dodecanoyl-DL-homoserine lactone (C12HSL);
   N-3-oxododecanoyl-L-homoserine lactone (3OC12HSL); or
   N-3-tetradecanoyl-DL-homoserine lactone (C14HSL).

3. The method of claim 1, wherein the γ-proteobacterium comprises a *Pseudomonas* species.

4. The method of claim 3, wherein the *Pseudomonas* species comprises *Pseudomonas aeruginosa*.

5. The method of claim 1, wherein the sample further comprises a short chain AHL, and wherein said method further comprises detecting no change in the amount of short chain AHL in the presence of the test agent as compared to the absence of the test agent.

6. The method of claim 5, wherein the short chain AHL comprises
   N-3-butanoyl-DL-homoserine lactone (C4HSL);
   N-3-hexanoyl-L-homoserine lactone (C6HSL);
   N-3-oxohexanoyl-L-homoserine lactone (3OC6HSL); or
   N-3-heptanoyl-DL-homoserine lactone (C7HSL).

7. The method of claim 1, wherein said modulating comprises increasing the AHL acylase activity.

8. The method of claim 7, wherein the agent increases AHL acylase gene expression, thereby increasing AHL acylase activity.

9. The method of claim 1, wherein the sample comprises a cell free sample.

10. The method of claim 9, wherein the AHL acylase comprises purified AHL acylase or an extract comprising a γ-proteobacterium.

11. The method of claim 10, wherein the γ-proteobacterium comprises a *Pseudomonas* species.

12. The method of claim 1, wherein the sample comprises a cell sample, or an extract of a cell, and wherein the AHL acylase is expressed in the cell.

13. The method of claim 12, wherein the cell sample is obtained from a subject having a γ-proteobacterium infection.

14. The method of claim 13, wherein the γ-proteobacterium comprises a *Pseudomonas* species.

15. The method of claim 1, wherein detecting a change in AHL acylase activity comprises measuring AHL levels in the sample.

16. The method of claim 15, wherein AHL levels are measured using mass spectroscopy.

17. The method of claim 1, wherein detecting a change in AHL acylase activity comprises measuring homoserine lactone (HSL) levels in the sample.

18. The method of claim 17, wherein HSL levels are measured using mass spectroscopy or thin-layer chromatography.

19. The method of claim 1, which is performed in a high throughput format.

20. The method of claim 1, wherein contacting said at least one test agent comprises contacting a plurality of different test agents each with their own sample.

21. The method of claim 20, wherein the different test agents comprise a library of test agents.

22. The method of claim 21, wherein the library of test agents comprises a combinatorial library of test agents.

23. The method of claim 22, wherein the combinatorial library comprises a random library, a biased library, or a variegated library of test agents.

* * * * *

UNITED STATES PATENT AND TRADEMARK OFFICE
CERTIFICATE OF CORRECTION

Page 1 of 1

PATENT NO. : 7,335,352 B1
APPLICATION NO. : 10/861224
DATED : February 26, 2008
INVENTOR(S) : Leadbetter and Huang It is certified that error appears in the above-identified patent and that said Letters Patent is hereby corrected as shown below:

In the Specification

Please delete the paragraph beginning on Line 20 of Column 1 and ending on Line 23 of Column 1 and replace with the following:

--This invention was made with government support under Grant No. GM007616 awarded by the National Institutes of Health, Grant No. N66001-02-1-8929 awarded by the U.S. Navy; Grant No. DBI0107908 awarded by the National Science Foundation and Grant No. CSREES 2001-01242 awarded by the United States Department of Agriculture. The government has certain rights in the invention.--

Signed and Sealed this
Twenty-first Day of April, 2015

Michelle K. Lee
*Director of the United States Patent and Trademark Office*

SEQUENCE LISTING

<160> NUMBER OF SEQ ID NOS: 9

<210> SEQ ID NO 1
<211> LENGTH: 2289
<212> TYPE: DNA
<213> ORGANISM: Pseudomonas PvdQ

<400> SEQUENCE: 1

```
atggggatgc gtaccgtact gaccggcctg gccggcatgc tgttgggttc gatgatgccg      60
gtccaggccg atatgccgcg gccgaccggg ctggccgcgg atatccgctg gaccgcctat     120
ggcgtgccgc acatccgggc caaggatgag cgcggcctgg gctatggcat cggctacgcc     180
tacgcgcgcg acaacgcctg cctgctggcc gaggagatcg tcaccgcgcg cggcgagcgg     240
gcgcgctatt cggcagcga gggcaagtcg tcggccgagc tggacaacct gccgtccgac     300
atcttctacg cctggctcaa ccaacccgag gcgctgcaag ccttctggca ggcgcagacg     360
cccgcggtac gccagttgct cgaaggctac gccgccggtt tcaaccgctt cctccgcgag     420
gccgacggca agaccaccag ttgccttggc cagccctggc tgcgggccat cgcgaccgat     480
gacctgctgc gcctgacccg gcgcctgctg gtcgaaggcg gggtcggcca gttcgccgac     540
gcgctggtgg ccgccgcgcc gcccggagcg gagaaggtcg ccttgagcgg cgagcaggcg     600
ttccaggtcg ccgagcagcg gcgccagcgc ttccgcctgg agcgcggcag caacgccatt     660
```

```
gccgttggca gcgaacgttc ggcggacggc aagggcatgc tcctggccaa cccgcacttc    720
ccctggaacg gcgcgatgcg tttctaccag atgcacctga ccattcccgg ccggctcgac    780
gtgatggggg cctcgctgcc cggcctgccg gtggtcaaca tcggcttcag ccgccacctg    840
gcctggaccc acacggtgga tacctccagc cacttcaccc tgtatcgcct ggcgctggac    900
ccgaaggacc cgcggcgcta cctggtcgac ggtcgttcgc tgccgctgga ggagaagtcc    960
gtcgcgatcg aggtgcgcgg cgccgacggc aagctgtcgc gcgtcgagca caaggtctac   1020
cagtcgatct acggcccgct ggtggtctgg cccggcaagc tggactggaa ccgcagcgag   1080
gcctatgcgc tgcgtgacgc caacctggag aacacccggg tactgcaaca gtggtactcg   1140
atcaaccagg ccagcgacgt cgccgacctg cgccggcgcg tcgaggcgct acaggggatc   1200
ccctgggtca cacccctggc cgcggacgag cagggcaacg ccctgtacat gaaccagtcg   1260
gtggtgccct acctgaagcc ggaactgatt cccgcctgcg ccattccgca actggtcgcc   1320
gaaggcctgc cggccctcca ggggcaggac agccgctgtg cctggagtcg cgacccggcc   1380
gcggcccagg ctggcatcac cccggcggcg caactgccgg tgctgttgcg cagggacttc   1440
gtgcagaact ccaacgacag cgcctggctg accaacccgg cgagcccgct gcagggcttc   1500
tcgcccctgg tcagccagga aagcccatc ggtccgcggg cgcgctacgc cctgagccgg   1560
ctacagggca gcagccgct ggaggcgaag acgctcgagg agatggtcac cgccaaccat   1620
gtcttcagcg ccgaccaggt gctgccggac ctgctccgcc tgtgccgcga caaccagggc   1680
gagaagtccc ttgcccgcgc ctgcgcggcc ctggcgcagt gggaccgtgg cgccaacctc   1740
gacagcggca gcggcttcgt ctacttccag cgcttcatgc aacgcttcgc cgaactcgac   1800
ggcgcgtgga aggaaccgtt cgatgcgcaa cgtcccctgg atacgccgca aggcatcgcc   1860
ctcgaccggc cgcaggtggc gacccaggtg cgccaggcgc tggcggacgc ggcggcggag   1920
gtggagaaga gcgggattcc cgacggcgcg cgctggggcg acctgcaagt gagcacccgt   1980
ggccaggaac gcatcgcgat cccggcggc gatggccatt cgggtcta caacgcgatc   2040 cagagcgtcc gcaagggcga ccacctggag gtggtcggcg cactagcta catccagctg   2100 gtgaccttcc ccgaggaagg gcccaaggct cgcgggttgc tggctttctc ccagtccagc   2160
gatccgcgct cgccgcacta ccgcgaccag accgagctgt tttcccgcca gcaatggcag   2220
accttgccgt tcagcgacag gcagatcgac gccgacccgc aactgcaacg gctaagcatt   2280
cgcgaatga                                                            2289
```

<210> SEQ ID NO 2
<211> LENGTH: 762
<212> TYPE: PRT
<213> ORGANISM: Pseudomonas PvdQ

<400> SEQUENCE: 2

Met Gly Met Arg Thr Val Leu Thr Gly Leu Ala Gly Met Leu Leu Gly
1               5                   10                  15

Ser Met Met Pro Val Gln Ala Asp Met Pro Arg Pro Thr Gly Leu Ala
            20                  25                  30

Ala Asp Ile Arg Trp Thr Ala Tyr Gly Val Pro His Ile Arg Ala Lys
        35                  40                  45

Asp Glu Arg Gly Leu Gly Tyr Gly Ile Gly Tyr Ala Tyr Ala Arg Asp
    50                  55                  60

Asn Ala Cys Leu Leu Ala Glu Glu Ile Val Thr Ala Arg Gly Glu Arg
65                  70                  75                  80

-continued

```
Ala Arg Tyr Phe Gly Ser Glu Gly Lys Ser Ala Glu Leu Asp Asn
                85                  90                  95

Leu Pro Ser Asp Ile Phe Tyr Ala Trp Leu Asn Gln Pro Glu Ala Leu
            100                 105                 110

Gln Ala Phe Trp Gln Ala Gln Thr Pro Ala Val Arg Gln Leu Leu Glu
            115                 120                 125

Gly Tyr Ala Ala Gly Phe Asn Arg Phe Leu Arg Glu Ala Asp Gly Lys
        130                 135                 140

Thr Thr Ser Cys Leu Gly Gln Pro Trp Leu Arg Ala Ile Ala Thr Asp
145                 150                 155                 160

Asp Leu Leu Arg Leu Thr Arg Arg Leu Leu Val Glu Gly Gly Val Gly
                165                 170                 175

Gln Phe Ala Asp Ala Leu Val Ala Ala Pro Pro Gly Ala Glu Lys
            180                 185                 190

Val Ala Leu Ser Gly Glu Gln Ala Phe Gln Val Ala Glu Gln Arg Arg
        195                 200                 205

Gln Arg Phe Arg Leu Glu Arg Gly Ser Asn Ala Ile Ala Val Gly Ser
    210                 215                 220

Glu Arg Ser Ala Asp Gly Lys Gly Met Leu Leu Ala Asn Pro His Phe
225                 230                 235                 240

Pro Trp Asn Gly Ala Met Arg Phe Tyr Gln Met His Leu Thr Ile Pro
                245                 250                 255

Gly Arg Leu Asp Val Met Gly Ala Ser Leu Pro Gly Leu Pro Val Val
            260                 265                 270

Asn Ile Gly Phe Ser Arg His Leu Ala Trp Thr His Thr Val Asp Thr
        275                 280                 285

Ser Ser His Phe Thr Leu Tyr Arg Leu Ala Leu Asp Pro Lys Asp Pro
    290                 295                 300

Arg Arg Tyr Leu Val Asp Gly Arg Ser Leu Pro Leu Glu Glu Lys Ser
305                 310                 315                 320

Val Ala Ile Glu Val Arg Gly Ala Asp Gly Lys Leu Ser Arg Val Glu
                325                 330                 335

His Lys Val Tyr Gln Ser Ile Tyr Gly Pro Leu Val Val Trp Pro Gly
            340                 345                 350

Lys Leu Asp Trp Asn Arg Ser Glu Ala Tyr Ala Leu Arg Asp Ala Asn
        355                 360                 365

Leu Glu Asn Thr Arg Val Leu Gln Gln Trp Tyr Ser Ile Asn Gln Ala
    370                 375                 380

Ser Asp Val Ala Asp Leu Arg Arg Val Glu Ala Leu Gln Gly Ile
385                 390                 395                 400

Pro Trp Val Asn Thr Leu Ala Ala Asp Glu Gln Gly Asn Ala Leu Tyr
                405                 410                 415

Met Asn Gln Ser Val Val Pro Tyr Leu Lys Pro Glu Leu Ile Pro Ala
            420                 425                 430

Cys Ala Ile Pro Gln Leu Val Ala Glu Gly Leu Pro Ala Leu Gln Gly
        435                 440                 445

Gln Asp Ser Arg Cys Ala Trp Ser Arg Asp Pro Ala Ala Gln Ala
    450                 455                 460

Gly Ile Thr Pro Ala Ala Gln Leu Pro Val Leu Leu Arg Arg Asp Phe
465                 470                 475                 480

Val Gln Asn Ser Asn Asp Ser Ala Trp Leu Thr Asn Pro Ala Ser Pro
                485                 490                 495

Leu Gln Gly Phe Ser Pro Leu Val Ser Gln Glu Lys Pro Ile Gly Pro
```

-continued

```
              500                 505                 510
Arg Ala Arg Tyr Ala Leu Ser Arg Leu Gln Gly Lys Gln Pro Leu Glu
            515                 520                 525

Ala Lys Thr Leu Glu Glu Met Val Thr Ala Asn His Val Phe Ser Ala
        530                 535                 540

Asp Gln Val Leu Pro Asp Leu Leu Arg Leu Cys Arg Asp Asn Gln Gly
545                 550                 555                 560

Glu Lys Ser Leu Ala Arg Ala Cys Ala Ala Leu Ala Gln Trp Asp Arg
                565                 570                 575

Gly Ala Asn Leu Asp Ser Gly Ser Gly Phe Val Tyr Phe Gln Arg Phe
            580                 585                 590

Met Gln Arg Phe Ala Glu Leu Asp Gly Ala Trp Lys Glu Pro Phe Asp
        595                 600                 605

Ala Gln Arg Pro Leu Asp Thr Pro Gln Gly Ile Ala Leu Asp Arg Pro
    610                 615                 620

Gln Val Ala Thr Gln Val Arg Gln Ala Leu Ala Asp Ala Ala Ala Glu
625                 630                 635                 640

Val Glu Lys Ser Gly Ile Pro Asp Gly Ala Arg Trp Gly Asp Leu Gln
                645                 650                 655

Val Ser Thr Arg Gly Gln Glu Arg Ile Ala Ile Pro Gly Gly Asp Gly
            660                 665                 670

His Phe Gly Val Tyr Asn Ala Ile Gln Ser Val Arg Lys Gly Asp His
        675                 680                 685

Leu Glu Val Val Gly Gly Thr Ser Tyr Ile Gln Leu Val Thr Phe Pro
    690                 695                 700

Glu Glu Gly Pro Lys Ala Arg Gly Leu Leu Ala Phe Ser Gln Ser Ser
705                 710                 715                 720

Asp Pro Arg Ser Pro His Tyr Arg Asp Gln Thr Glu Leu Phe Ser Arg
                725                 730                 735

Gln Gln Trp Gln Thr Leu Pro Phe Ser Asp Arg Gln Ile Asp Ala Asp
            740                 745                 750

Pro Gln Leu Gln Arg Leu Ser Ile Arg Glu
        755                 760
```

<210> SEQ ID NO 3
<211> LENGTH: 2544
<212> TYPE: DNA
<213> ORGANISM: Pseudomonas PA1032

<400> SEQUENCE: 3

```
atggcctcgc cagccttcat gcgtttctct cccgttgcg gcgccgccgc ggccttcggc    60
accctcctgg gctggccgg ttgccagtcc tggctcgacg atcgctacgc cgacagcctg   120
ccgccgacct ccggcgtaca accgatcaag ggcctggcgc aaaacgtatc gatccggcgc   180
aacgcgctgg gcatgccact gatcgaaacc ggcaccttcc atgacgcgct gttcgccctg   240
ggctacgtac acgcctccga ccgcctgagc cagatggtca gcctgcgcct gctggcccag   300
ggacggctgg ccgagatggt cggccccggc gcgctggaga tcgaccgttt catgcgtacc   360
gtgaacctgc gccaggctgc ggagatccag tacaggaacg cctcgccgcg cctgcaacgc   420
ttcttcgagg tctacgcgcg cggggtcaac gcctacctgt atcgctatcg cgacaagctg   480
ccgatggacc tggcccagtc cggctaccgt ccggaatact ggaagcccga ggactcggcg   540
ctggtcttcg ccctgctcaa cttcggcctg gcggtgaacc tgcaggaaga aatcgcctcg   600
ctgacgctcg cgcagaaggt cggcagcgac aagctggcct ggctgacgcc gacctatccc   660
```

-continued

```
gacgaaaacc tgccgttcga cgaggcggaa aagctcaagg gcctgcgcct ggacgggcag      720
gttcccggcc tcgcgggcgt cgagggcgcg gcgcggcagg tcgcagcgct gagcatgctc      780
ggggtcgccg cctcgaacaa ctgggctatc gcgccgcaac gcagccgcag cggcaagagc      840
ctgatggcca acgacaccca cctgccgctg agcatgccgt cggtgtggaa ctacgtgcag      900
atccgctcgc ccaagtacca ggccgcgggc gtttccatcg ccgtctgcc gggcgtggtg       960
gcgggcttca cggcaagct ggcctggggc atgaccatgg tcctgggcga caaccaggat      1020
ctctacctgg aacagctgcg acgccagggc aaccggctct attacctggc cgacggcaag      1080
tggcagccaa cccgcgaacg ccaggaaacc ttcttcatca agggccagcg gccgatccgc      1140
gaggtcatcc acgaaacccg ccatggcccg ctgctcaaca gcgccctggg cgagcgcaag      1200
aacatcctcc agccgctgcc gctgaagagc ggctacggac tggcctaccg gagcatccag      1260
caggaagccg acaagaccct ggacggcttc ttcgacctgt cgcgggccaa gaccatcgag      1320
caggccttcg acgccacccg cgagattcgc gcgatgccgc tgaacatcgt gttcgccgac      1380
gaaaagcaca tcggctggca ggtcaccgga cgctatccga accgcaagga aggtcgtggc      1440
ctgctgccct cccctggctg ggacggccgc tacgactggg atggctatgc cgacccgatc      1500
ctccacccgt ccgaccagga cccgcagcag ggctggctgg gtaccgccaa ccaccgcacc      1560
gtgcagcccg gctacggcgc ccagttgtcc aattcctggt actacccgga gcgcgccgag      1620
cgcatcgccc agctcgccgg tgccagcaag agccacgaca cccagagcat gatccgcatg      1680
cagtacgacc agacctcgct gttcgtcgcc aagctgcaag ccatgttcga caatcccggc      1740
atggcgctgc cgctgcgcca ggccatcgac gccttgccgg aggcgcaacg cagccgggcg      1800
cgggaggcct acgaccggct gatggcgttc acggcaagc tgacagccag ctccagcgac      1860
gccgcgctgt acggcgcctt cctccacgag agcgccaggc agatattcct cgacgagcta      1920
ggaccggagg acgccctgc ctggaaagcc ttcgtcgaga ccgccaacct ctcctactcg      1980
gcgcaagccg accacctgct cgggcgcgac gacagtccgt tctgggacga taccgcact      2040
ccgcagaagg aggacaagcc ggcaatcctc gcgcgcagcc tcgccgccgc cgtggagttc      2100
tgcgaacagc gactggggag cgagcgcaag gcctggcaat ggggcaagct gcacacctac      2160
gaatggcaga cgacagctc gaaaatggcc cctacctgg gcgccggcga gcgcgccgga       2220
ctcggcgcga tcaagggcta tctcgatcgc ggaccctatc cggccggcgg cgaccacacc      2280
acgctggacg tatcgcccta cggctggggc caggacttcg acacttggct gatcccggcg      2340
atgcggctga tcgtcgactt cggccagagc gaaccgatga tcggcgtgaa cagcagcggc      2400
caatccggca atccggccag cccgcactac gccgacggta tcgacgcctg gctcaagggg      2460
cgctacgtta gcttcccgtt ccagccacag aacctcgatc gcgtttacgg caacaagcgg      2520
ctgacgctca ctcccgctcg ctga                                             2544
```

<210> SEQ ID NO 4
<211> LENGTH: 847
<212> TYPE: PRT
<213> ORGANISM: Pseudomonas PA1032

<400> SEQUENCE: 4

```
Met Ala Ser Pro Ala Phe Met Arg Phe Leu Pro Arg Cys Gly Ala Ala
1               5                   10                  15

Ala Ala Phe Gly Thr Leu Leu Gly Leu Ala Gly Cys Gln Ser Trp Leu
            20                  25                  30
```

-continued

```
Asp Asp Arg Tyr Ala Asp Ser Leu Pro Pro Thr Ser Gly Val Gln Pro
        35                  40                  45

Ile Lys Gly Leu Ala Gln Asn Val Ser Ile Arg Arg Asn Ala Leu Gly
        50                  55                  60

Met Pro Leu Ile Glu Thr Gly Thr Phe His Asp Ala Leu Phe Ala Leu
65                  70                  75                  80

Gly Tyr Val His Ala Ser Asp Arg Leu Ser Gln Met Val Ser Leu Arg
                85                  90                  95

Leu Leu Ala Gln Gly Arg Leu Ala Glu Met Val Gly Pro Gly Ala Leu
                100                 105                 110

Glu Ile Asp Arg Phe Met Arg Thr Val Asn Leu Arg Gln Ala Ala Glu
        115                 120                 125

Ile Gln Tyr Arg Asn Ala Ser Pro Arg Leu Gln Arg Phe Phe Glu Val
        130                 135                 140

Tyr Ala Arg Gly Val Asn Ala Tyr Leu Tyr Arg Tyr Arg Asp Lys Leu
145                 150                 155                 160

Pro Met Asp Leu Ala Gln Ser Gly Tyr Arg Pro Glu Tyr Trp Lys Pro
                165                 170                 175

Glu Asp Ser Ala Leu Val Phe Ala Leu Leu Asn Phe Gly Leu Ala Val
                180                 185                 190

Asn Leu Gln Glu Glu Ile Ala Ser Leu Thr Leu Ala Gln Lys Val Gly
        195                 200                 205

Ser Asp Lys Leu Ala Trp Leu Thr Pro Thr Tyr Pro Asp Glu Asn Leu
        210                 215                 220

Pro Phe Asp Glu Ala Glu Lys Leu Lys Gly Leu Arg Leu Asp Gly Gln
225                 230                 235                 240

Val Pro Gly Leu Ala Gly Val Glu Gly Ala Arg Gln Val Ala Ala
                245                 250                 255

Leu Ser Met Leu Gly Val Ala Ala Ser Asn Asn Trp Ala Ile Ala Pro
                260                 265                 270

Gln Arg Ser Arg Ser Gly Lys Ser Leu Met Ala Asn Asp Thr His Leu
        275                 280                 285

Pro Leu Ser Met Pro Ser Val Trp Asn Tyr Val Gln Ile Arg Ser Pro
        290                 295                 300

Lys Tyr Gln Ala Ala Gly Val Ser Ile Ala Gly Leu Pro Gly Val Val
305                 310                 315                 320

Ala Gly Phe Asn Gly Lys Leu Ala Trp Gly Met Thr Met Val Leu Gly
                325                 330                 335

Asp Asn Gln Asp Leu Tyr Leu Glu Gln Leu Arg Arg Gln Gly Asn Arg
                340                 345                 350

Leu Tyr Tyr Leu Ala Asp Gly Lys Trp Gln Pro Thr Arg Glu Arg Gln
        355                 360                 365

Glu Thr Phe Phe Ile Lys Gly Gln Arg Pro Ile Arg Glu Val Ile His
        370                 375                 380

Glu Thr Arg His Gly Pro Leu Leu Asn Ser Ala Leu Gly Glu Arg Lys
385                 390                 395                 400

Asn Ile Leu Gln Pro Leu Pro Leu Lys Ser Gly Tyr Gly Leu Ala Tyr
                405                 410                 415

Arg Ser Ile Gln Gln Glu Ala Asp Lys Thr Leu Asp Gly Phe Phe Asp
        420                 425                 430

Leu Ser Arg Ala Lys Thr Ile Glu Gln Ala Phe Asp Ala Thr Arg Glu
        435                 440                 445

Ile Arg Ala Met Pro Leu Asn Ile Val Phe Ala Asp Glu Lys His Ile
```

-continued

```
            450                 455                 460
Gly Trp Gln Val Thr Gly Arg Tyr Pro Asn Arg Lys Glu Gly Arg Gly
465                 470                 475                 480

Leu Leu Pro Ser Pro Gly Trp Asp Gly Arg Tyr Asp Trp Asp Gly Tyr
                485                 490                 495

Ala Asp Pro Ile Leu His Pro Ser Asp Gln Asp Pro Gln Gln Gly Trp
            500                 505                 510

Leu Gly Thr Ala Asn His Arg Thr Val Gln Pro Gly Tyr Gly Ala Gln
            515                 520                 525

Leu Ser Asn Ser Trp Tyr Tyr Pro Glu Arg Ala Glu Arg Ile Ala Gln
        530                 535                 540

Leu Ala Gly Ala Ser Lys Ser His Asp Thr Gln Ser Met Ile Arg Met
545                 550                 555                 560

Gln Tyr Asp Gln Thr Ser Leu Phe Val Ala Lys Leu Gln Ala Met Phe
                565                 570                 575

Asp Asn Pro Gly Met Ala Leu Pro Leu Arg Gln Ala Ile Asp Ala Leu
            580                 585                 590

Pro Glu Ala Gln Arg Ser Arg Ala Arg Glu Ala Tyr Asp Arg Leu Met
        595                 600                 605

Ala Phe Asp Gly Lys Leu Thr Ala Ser Ser Asp Ala Ala Leu Tyr
610                 615                 620

Gly Ala Phe Leu His Glu Ser Ala Arg Gln Ile Phe Leu Asp Glu Leu
625                 630                 635                 640

Gly Pro Glu Asp Gly Pro Ala Trp Lys Ala Phe Val Glu Thr Ala Asn
                645                 650                 655

Leu Ser Tyr Ser Ala Gln Ala Asp His Leu Leu Gly Arg Asp Asp Ser
            660                 665                 670

Pro Phe Trp Asp Asp Thr Arg Thr Pro Gln Lys Glu Asp Lys Pro Ala
        675                 680                 685

Ile Leu Ala Arg Ser Leu Ala Ala Val Glu Phe Cys Glu Gln Arg
        690                 695                 700

Leu Gly Ser Glu Arg Lys Ala Trp Gln Trp Gly Lys Leu His Thr Tyr
705                 710                 715                 720

Glu Trp Gln Ser Asp Ser Ser Lys Met Ala Pro Tyr Leu Gly Ala Gly
                725                 730                 735

Glu Arg Ala Gly Leu Gly Ala Ile Lys Gly Tyr Leu Asp Arg Gly Pro
            740                 745                 750

Tyr Pro Ala Gly Gly Asp His Thr Thr Leu Asp Val Ser Ala Tyr Gly
        755                 760                 765

Trp Gly Gln Asp Phe Asp Thr Trp Leu Ile Pro Ala Met Arg Leu Ile
        770                 775                 780

Val Asp Phe Gly Gln Ser Glu Pro Met Ile Gly Val Asn Ser Ser Gly
785                 790                 795                 800

Gln Ser Gly Asn Pro Ala Ser Pro His Tyr Ala Asp Gly Ile Asp Ala
                805                 810                 815

Trp Leu Lys Gly Arg Tyr Val Ser Phe Pro Phe Gln Pro Gln Asn Leu
            820                 825                 830

Asp Arg Val Tyr Gly Asn Lys Arg Leu Thr Leu Thr Pro Ala Arg
        835                 840                 845

<210> SEQ ID NO 5
<211> LENGTH: 841
<212> TYPE: PRT
<213> ORGANISM: Pseudomonas - alternative PA1032
```

<400> SEQUENCE: 5

```
Met Arg Phe Leu Pro Arg Cys Gly Ala Ala Ala Phe Gly Thr Leu
1               5                   10                  15

Leu Gly Leu Ala Gly Cys Gln Ser Trp Leu Asp Asp Arg Tyr Ala Asp
            20                  25                  30

Ser Leu Pro Pro Thr Ser Gly Val Gln Pro Ile Lys Gly Leu Ala Gln
            35                  40                  45

Asn Val Ser Ile Arg Arg Asn Ala Leu Gly Met Pro Leu Ile Glu Thr
        50                  55                  60

Gly Thr Phe His Asp Ala Leu Phe Ala Leu Gly Tyr Val His Ala Ser
65              70                  75                  80

Asp Arg Leu Ser Gln Met Val Ser Leu Arg Leu Ala Gln Gly Arg
            85                  90                  95

Leu Ala Glu Met Val Gly Pro Gly Ala Leu Glu Ile Asp Arg Phe Met
            100                 105                 110

Arg Thr Val Asn Leu Arg Gln Ala Ala Glu Ile Gln Tyr Arg Asn Ala
            115                 120                 125

Ser Pro Arg Leu Gln Arg Phe Phe Glu Val Tyr Ala Arg Gly Val Asn
        130                 135                 140

Ala Tyr Leu Tyr Arg Tyr Arg Asp Lys Leu Pro Met Asp Leu Ala Gln
145             150                 155                 160

Ser Gly Tyr Arg Pro Glu Tyr Trp Lys Pro Glu Asp Ser Ala Leu Val
            165                 170                 175

Phe Ala Leu Leu Asn Phe Gly Leu Ala Val Asn Leu Gln Glu Glu Ile
            180                 185                 190

Ala Ser Leu Thr Leu Ala Gln Lys Val Gly Ser Asp Lys Leu Ala Trp
        195                 200                 205

Leu Thr Pro Thr Tyr Pro Asp Glu Asn Leu Pro Phe Asp Glu Ala Glu
        210                 215                 220

Lys Leu Lys Gly Leu Arg Leu Asp Gly Gln Val Pro Gly Leu Ala Gly
225             230                 235                 240

Val Glu Gly Ala Ala Arg Gln Val Ala Ala Leu Ser Met Leu Gly Val
            245                 250                 255

Ala Ala Ser Asn Asn Trp Ala Ile Ala Pro Gln Arg Ser Arg Ser Gly
            260                 265                 270

Lys Ser Leu Met Ala Asn Asp Thr His Leu Pro Leu Ser Met Pro Ser
        275                 280                 285

Val Trp Asn Tyr Val Gln Ile Arg Ser Pro Lys Tyr Gln Ala Ala Gly
        290                 295                 300

Val Ser Ile Ala Gly Leu Pro Gly Val Val Ala Gly Phe Asn Gly Lys
305             310                 315                 320

Leu Ala Trp Gly Met Thr Met Val Leu Gly Asp Asn Gln Asp Leu Tyr
            325                 330                 335

Leu Glu Gln Leu Arg Arg Gln Gly Asn Arg Leu Tyr Tyr Leu Ala Asp
            340                 345                 350

Gly Lys Trp Gln Pro Thr Arg Glu Arg Gln Glu Thr Phe Phe Ile Lys
        355                 360                 365

Gly Gln Arg Pro Ile Arg Glu Val Ile His Glu Thr Arg His Gly Pro
        370                 375                 380

Leu Leu Asn Ser Ala Leu Gly Glu Arg Lys Asn Ile Leu Gln Pro Leu
385             390                 395                 400

Pro Leu Lys Ser Gly Tyr Gly Leu Ala Tyr Arg Ser Ile Gln Gln Glu
```

-continued

```
                  405                 410                 415
Ala Asp Lys Thr Leu Asp Gly Phe Phe Asp Leu Ser Arg Ala Lys Thr
            420                 425                 430
Ile Glu Gln Ala Phe Asp Ala Thr Arg Glu Ile Arg Ala Met Pro Leu
            435                 440                 445
Asn Ile Val Phe Ala Asp Glu Lys His Ile Gly Trp Gln Val Thr Gly
            450                 455                 460
Arg Tyr Pro Asn Arg Lys Glu Gly Arg Gly Leu Leu Pro Ser Pro Gly
465                 470                 475                 480
Trp Asp Gly Arg Tyr Asp Trp Asp Gly Tyr Ala Asp Pro Ile Leu His
                485                 490                 495
Pro Ser Asp Gln Asp Pro Gln Gln Gly Trp Leu Gly Thr Ala Asn His
                500                 505                 510
Arg Thr Val Gln Pro Gly Tyr Gly Ala Gln Leu Ser Asn Ser Trp Tyr
            515                 520                 525
Tyr Pro Glu Arg Ala Glu Arg Ile Ala Gln Leu Ala Gly Ala Ser Lys
            530                 535                 540
Ser His Asp Thr Gln Ser Met Ile Arg Met Gln Tyr Asp Gln Thr Ser
545                 550                 555                 560
Leu Phe Val Ala Lys Leu Gln Ala Met Phe Asp Asn Pro Gly Met Ala
                565                 570                 575
Leu Pro Leu Arg Gln Ala Ile Asp Ala Leu Pro Glu Ala Gln Arg Ser
            580                 585                 590
Arg Ala Arg Glu Ala Tyr Asp Arg Leu Met Ala Phe Asp Gly Lys Leu
            595                 600                 605
Thr Ala Ser Ser Asp Ala Ala Leu Tyr Gly Ala Phe Leu His Glu
            610                 615                 620
Ser Ala Arg Gln Ile Phe Leu Asp Glu Leu Gly Pro Glu Asp Gly Pro
625                 630                 635                 640
Ala Trp Lys Ala Phe Val Glu Thr Ala Asn Leu Ser Tyr Ser Ala Gln
                645                 650                 655
Ala Asp His Leu Leu Gly Arg Asp Asp Ser Pro Phe Trp Asp Asp Thr
                660                 665                 670
Arg Thr Pro Gln Lys Glu Asp Lys Pro Ala Ile Leu Ala Arg Ser Leu
            675                 680                 685
Ala Ala Ala Val Glu Phe Cys Glu Gln Arg Leu Gly Ser Glu Arg Lys
            690                 695                 700
Ala Trp Gln Trp Gly Lys Leu His Thr Tyr Glu Trp Gln Ser Asp Ser
705                 710                 715                 720
Ser Lys Met Ala Pro Tyr Leu Gly Ala Gly Glu Arg Ala Gly Leu Gly
                725                 730                 735
Ala Ile Lys Gly Tyr Leu Asp Arg Gly Pro Tyr Pro Ala Gly Gly Asp
            740                 745                 750
His Thr Thr Leu Asp Val Ser Ala Tyr Gly Trp Gly Gln Asp Phe Asp
            755                 760                 765
Thr Trp Leu Ile Pro Ala Met Arg Leu Ile Val Asp Phe Gly Gln Ser
            770                 775                 780
Glu Pro Met Ile Gly Val Asn Ser Ser Gly Gln Ser Gly Asn Pro Ala
785                 790                 795                 800
Ser Pro His Tyr Ala Asp Gly Ile Asp Ala Trp Leu Lys Gly Arg Tyr
                805                 810                 815
Val Ser Phe Pro Phe Gln Pro Gln Asn Leu Asp Arg Val Tyr Gly Asn
            820                 825                 830
```

```
Lys Arg Leu Thr Leu Thr Pro Ala Arg
        835                 840

<210> SEQ ID NO 6
<211> LENGTH: 33
<212> TYPE: DNA
<213> ORGANISM: Artificial sequence
<220> FEATURE:
<223> OTHER INFORMATION: Amplification primer

<400> SEQUENCE: 6
aggccaagct tatgggggat gcgtaccgta ctg                                33

<210> SEQ ID NO 7
<211> LENGTH: 36
<212> TYPE: DNA
<213> ORGANISM: Artificial sequence
<220> FEATURE:
<223> OTHER INFORMATION: Amplification primer

<400> SEQUENCE: 7
gttatatagc ggccgctagg cattgcttat cattcg                             36

<210> SEQ ID NO 8
<211> LENGTH: 32
<212> TYPE: DNA
<213> ORGANISM: Artificial sequence
<220> FEATURE:
<223> OTHER INFORMATION: Amplification primer

<400> SEQUENCE: 8
aagaggacat atgggggatg cgtaccgtac tg                                 32

<210> SEQ ID NO 9
<211> LENGTH: 30
<212> TYPE: DNA
<213> ORGANISM: Artificial sequence
<220> FEATURE:
<223> OTHER INFORMATION: Amplification primer

<400> SEQUENCE: 9
ctaaagcttg gctgtgggcc gcctctatgg                                    30
```